(12) United States Patent
Eggenberger et al.

(10) Patent No.: US 6,996,455 B2
(45) Date of Patent: Feb. 7, 2006

(54) DISPENSING CABINET WITH UNIT DOSE DISPENSING DRAWER

(75) Inventors: Victor Eggenberger, North Versailles, PA (US); Kirk Young, Pittsburgh, PA (US); Allen Bowers, Pittsburgh, PA (US)

(73) Assignee: McKesson Automation Inc., Pittsburgh, PA (US)

(*) Notice: Subject to any disclaimer, the term of this patent is extended or adjusted under 35 U.S.C. 154(b) by 116 days.

(21) Appl. No.: 10/455,116

(22) Filed: Jun. 5, 2003

(65) Prior Publication Data

US 2003/0200007 A1 Oct. 23, 2003

Related U.S. Application Data

(62) Division of application No. 09/998,515, filed on Nov. 30, 2001, now Pat. No. 6,785,589.

(51) Int. Cl.
*G06F 17/00* (2006.01)

(52) U.S. Cl. .................. 700/231; 700/236; 700/237; 700/242

(58) Field of Classification Search .......... 700/231, 700/236, 237, 240, 241, 244, 242
See application file for complete search history.

(56) References Cited

U.S. PATENT DOCUMENTS

| | | | |
|---|---|---|---|
| 4,019,793 A | 4/1977 | Gerding | |
| 4,114,965 A | 9/1978 | Oye et al. | |
| 4,127,311 A | 11/1978 | Weiman | |
| 4,588,237 A | 5/1986 | Marder | |
| 4,811,764 A | 3/1989 | McLaughlin | |
| 4,813,753 A | 3/1989 | Relyea | |
| 4,847,764 A | 7/1989 | Halvorson | |
| 5,004,306 A | 4/1991 | Oshida | |
| 5,014,875 A | 5/1991 | McLaughlin et al. | |
| 5,087,107 A | 2/1992 | Fumanelli | |
| 5,139,321 A | 8/1992 | Beardsley | |
| 5,143,432 A | 9/1992 | Ohshima et al. | |
| 5,159,581 A | 10/1992 | Agans | |
| 5,200,891 A | 4/1993 | Kehr et al. | |
| 5,346,297 A | 9/1994 | Colson, Jr. et al. | |
| 5,445,294 A | 8/1995 | Gardner et al. | |
| 5,520,450 A | 5/1996 | Colson, Jr. et al. | |
| 5,745,366 A | 4/1998 | Higham et al. | |
| 5,883,806 A * | 3/1999 | Meador et al. ............. 700/244 |
| 5,905,653 A | 5/1999 | Higham et al. | |
| 5,927,540 A | 7/1999 | Godlewski | |
| 6,011,999 A | 1/2000 | Holmes | |
| 6,019,249 A | 2/2000 | Michael et al. | |
| 6,021,392 A | 2/2000 | Lester et al. | |
| 6,065,819 A | 5/2000 | Holmes et al. | |
| 6,109,774 A * | 8/2000 | Holmes et al. ............. 700/231 |
| 6,112,502 A | 9/2000 | Frederick et al. | |
| 6,116,461 A | 9/2000 | Broadfield et al. | |
| 6,532,399 B2 * | 3/2003 | Mase ........................ 700/237 |
| 6,640,159 B2 * | 10/2003 | Holmes et al. ............. 700/244 |

* cited by examiner

*Primary Examiner*—Gene O. Crawford
(74) *Attorney, Agent, or Firm*—Thorp Reed & Armstrong, LLP

(57) ABSTRACT

A drawer for use in a dispensing cabinet is comprised of a tray movable between an open position and a closed position. An insert, approximately the length of the tray, is carried by the tray and defines the volume of the drawer. A lockable or sealable lid is carried by the insert. A release mechanism is provided to connect the insert to the tray in a manner that allows the insert to be easily disconnected from the tray. Removal of the insert enables inserts to be swapped so that inserts from which inventory has been depleted can be replaced with stocked inserts. A dispensing cabinet and a method of restocking the cabinet are also disclosed.

6 Claims, 32 Drawing Sheets

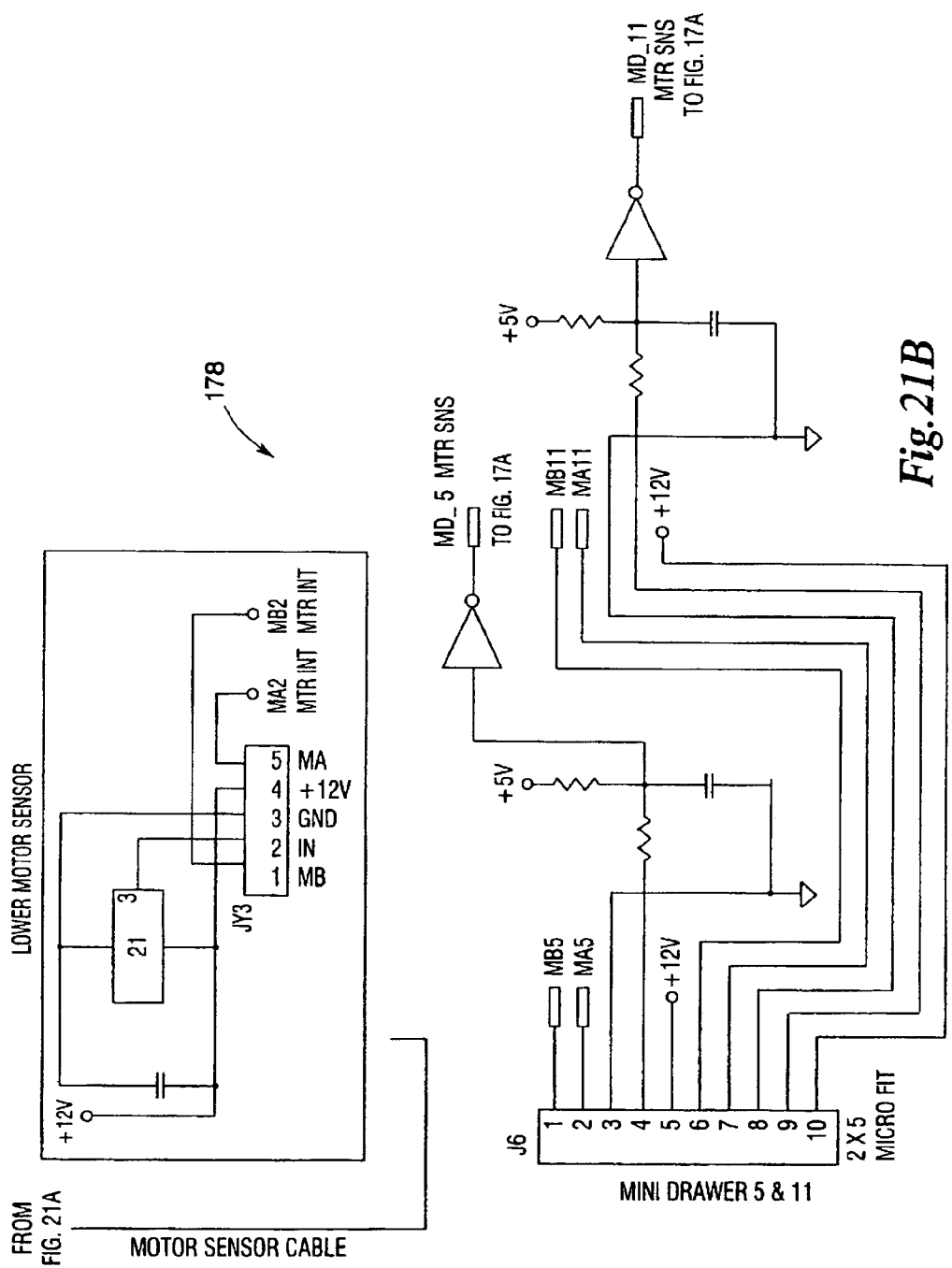

DISPENSING CABINET WITH UNIT DOSE DISPENSING DRAWER

CROSS-REFERENCE TO RELATED APPLICATIONS

The present invention is a divisional of U.S. application Ser. No. 09/998,515 entitled "Dispensing Cabinet with Unit Dose Dispensing Drawer" filed 30 Nov. 2001, now U.S. Pat. No. 6,785,589 and assigned to the same assignee as the present invention.

BACKGROUND OF THE INVENTION

1. Field of the Invention

The present invention is directed to dispensing cabinets and, more particularly, to dispensing cabinets having drawers of the type which are opened and closed under the control of a computer to control access to the contents of the drawer.

2. Description of the Background

In large medical facilities, inventories of medical supplies are normally held in centralized storage locations or pharmacies which are often far removed from decentralized storage locations. It is at the decentralized storage locations, e.g. a nurses station, that dispenses for patients are typically performed. To facilitate dispensing of medications and supplies for patients, a variety of dispensing systems have been proposed. For example, several dispensing systems have been proposed which employ a cart or cabinet which is located at the decentralized location.

Of particular interest to the present invention are dispensing systems which dispense pharmaceuticals and other items which require close monitoring and control. A variety of schemes have been proposed for providing secured access to pharmaceuticals that are held within such dispensing systems, including locking the pharmaceuticals within the carts or by allowing access to only one item at a time, commonly referred to as "single dose" or "unit dose" dispensing.

One such system is described in U.S. Pat. No. 5,014,875 titled "Medication Dispenser Station." That system comprises a multiple-drawer cabinet for holding pharmaceuticals, with each drawer containing a covered, multiple-compartment carousel. Access to each drawer and each carousel compartment is controlled to allow access to the contents after a predetermined code or other information has been entered into a controller.

Another system is described in U.S. Pat. No. 4,847,764 titled "System for Dispensing Drugs in Health Care Institutions." That dispensing system involves a computer system connected to a number of remote medication dispensers. The computer system includes software for, among other things, controlling access to the medications, identifying potentially dangerous drug interactions, and assisting with inventory control. The remote medication dispensers comprise a number of cabinets, with each cabinet holding a number of unit dose medication packages.

U.S. Pat. No. 5,927,540 titled "Controlled Dispensing System and Method" discloses apparatus and methods for dispensing articles in a controlled manner. In one embodiment, the invention provides an apparatus comprising a cabinet defining an enclosure. At least one drawer is attached to the cabinet and is configured to slide in and out of the cabinet. The drawer contains an array of compartments. At least one lid is attached to the drawer and is configured to slide forward and backward with respect to the drawer. Each drawer further includes a locking mechanism which may engage the lid at selective locations along the lid. With this arrangement, the locking mechanism may engage the lid to prevent movement of the lid relative to the drawer after a certain compartment has been exposed. Each drawer further includes a distance sensor for detecting the distance traveled by the lid relative to the drawer. A controller is placed in communication with both the locking mechanism and the distance sensor. The controller sends a signal to actuate the locking mechanism after the lid has been moved to expose a desired compartment. In that manner, the lid may be moved to allow access to a compartment containing a desired article or medical supply. The locking mechanism then engages the lid to prevent further movement of the lid, thereby preventing access to additional compartments.

U.S. Pat. No. 6,109,774 titled "Drawer Operating System" discloses a drawer operating system for allowing graduated access to consecutively spaced bins, partitioned in a drawer, so that access to the bins is controlled. The invention is housed in the rear of each drawer. It tracks the previous activity of the drawer and, when later accessed, allows the drawer to be pulled open to a length that will expose the contents of a bin either not emptied in previous openings or not uncovered in previous openings, retaining the other item-filled bins inside the cabinet and secure from access. In the preferred embodiment, the drawer is driven from its fully-closed position to a slightly-opened position of one inch or so to indicate to the user that this particular drawer may be opened further by merely pulling it outward. When the drawer is later pushed toward its closed position, it is stopped short of full closure and subsequently slowly driven closed into a locked position in the cabinet. This latter feature prevents "slamming" of the drawers into the cabinet and reduces the potential for damage to the contents therein.

While such systems provide for unit dose dispensing, the need exists for a unit dose dispensing cabinet that provides a means of accessing the medications in the event of a power failure or the need arises to override the computer controlling the cabinet. Additionally, it is desirable for the dispensing cabinet to be refilled or restocked in a convenient manner that reduces the likelihood that a restocking error will occur.

SUMMARY OF THE PRESENT INVENTION

One aspect of the present invention is a drawer for use in a dispensing cabinet. The drawer is comprised of a tray movable between an open position and a closed position. An insert, approximately the length of the tray, is carried by the tray and defines the volume of the drawer. A lockable lid, i.e., mechanically lockable or sealable with an adhesive seal, is carried by the insert. A release mechanism is provided to connect the insert to the tray in a manner that allows the insert to be easily disconnected from the tray. Removal of the insert enables inserts to be swapped so that inserts from which inventory has been depleted can be replaced with stocked inserts. Eliminating the need to transfer inventory from a restocking package to the insert eliminates the possibility of errors occurring from such a transfer.

Another aspect of the present invention is a dispensing cabinet having unit dose drawers of the type previously described. The dispensing cabinet comprises an input device, an output device and a computer connected to the input and output devices. A cabinet has a plurality of drawers, at least one of the drawers being a unit-dose dispensing drawer capable of dispensing a unit-dose. Each unit-dose dispensing drawer is comprised of a plurality of individual drawers, each individual drawer comprising a tray drivable between an open position and a closed position. An insert is carried by the tray. The insert defines one or more individual compartments each having a lockable lid. The insert is approximately the length of the tray and defines the volume of the drawer. A release mechanism is provided for connecting the insert to the tray. A self locking worm gear driven by a motor is connected to the tray through a clutch to provide a mechanism for driving the tray. During normal operation, the friction provided by the worm gear renders the drawers unmovable unless they are driven by the motor. In the event of a power failure or other problem, the clutch can be used to disengage the tray from the worm gear so that the drawers can be opened and closed.

Another aspect of the present invention is a method of restocking a unit dose drawer of a dispensing cabinet. The method is comprised of the steps of releasing a first insert that defines the volume of an individual drawer from a tray, connecting a filled insert to the tray from which the first insert has been removed, and unlocking or unsealing the lid of the filled insert. The first insert may then be delivered to a storage location for filling. After filling, the lid is locked and the filled first insert is delivered to a dispensing cabinet.

The present invention provides a convenient apparatus and method of refilling or restocking a dispensing cabinet in a manner that reduces the possibility of errors. The cabinet can be operated in such a manner that the drawers of the dispensing cabinet may be manually operated in the event of a power failure or problem with the cabinet. Those, and other advantages and benefits, will be apparent from the Description of the Preferred Embodiments herein below.

BRIEF DESCRIPTION OF THE DRAWINGS

For the present invention to be easily understood and readily practiced, the present invention will now be described, for purposes of illustration and not limitation, in conjunction with the following figures, wherein.

DESCRIPTION OF THE PREFERRED EMBODIMENTS

Figure 1:
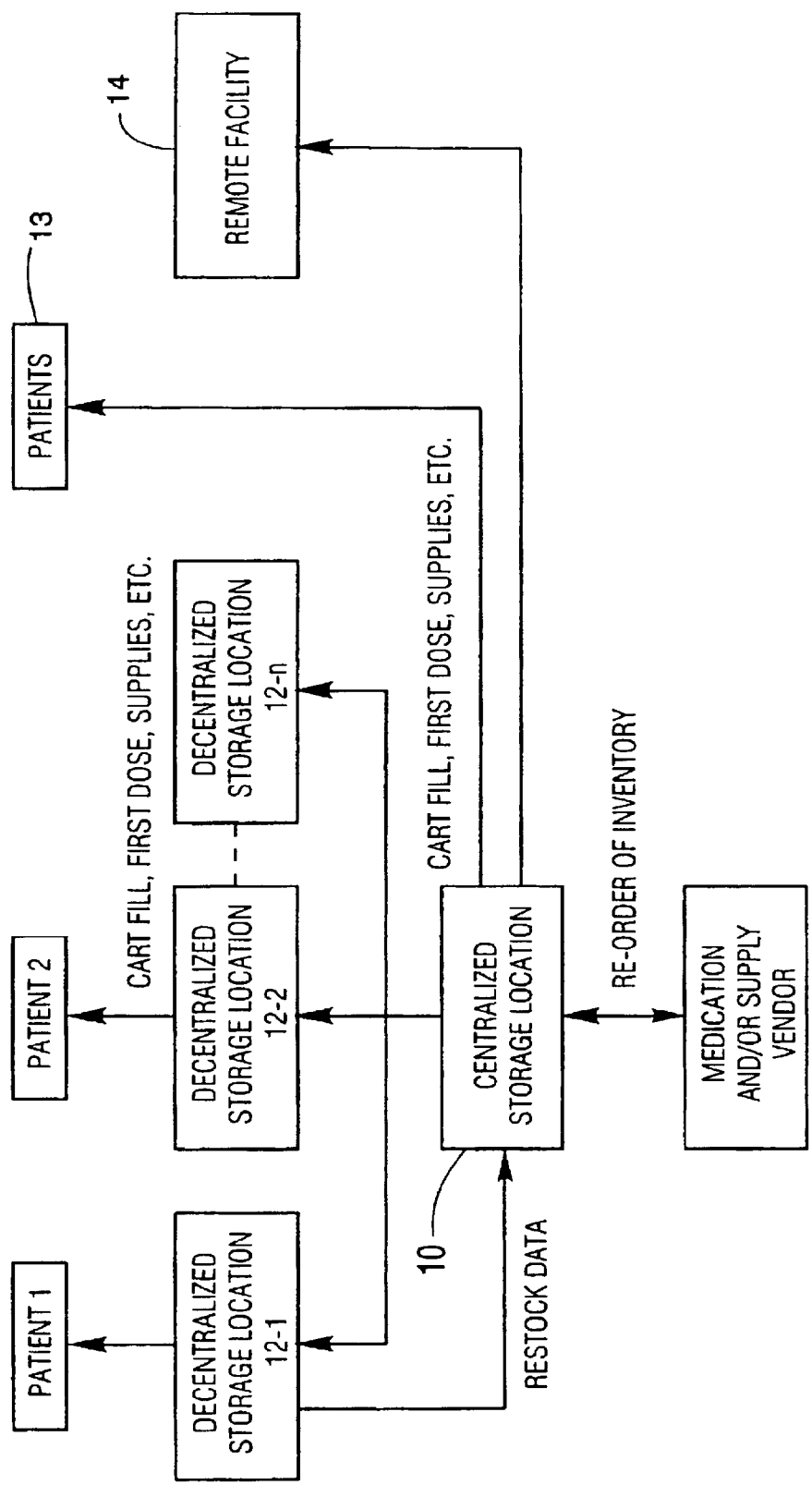
FIG. 1 is a diagram illustrating the relationship between a centralized storage location and a plurality of decentralized storage locations.

FIG. 1 is a diagram illustrating the relationship between a centralized storage location 10 and various inventory destinations, including a plurality of decentralized storage locations 12-1, 12-2 through 12-n, patients 13, and a remote facility 14. Each of the decentralized storage locations 12-1 through 12-n is capable of dispensing items stored at the location. The items may include medications, controlled medical supplies, medical supplies or items of a nature consistent with the facility in which the system illustrated in FIG. 1 is located. Items may be dispensed directly from centralized storage location 10 to patients 13, or from the centralized storage location 10 to a remote facility 14. Data typically flows from the decentralized storage locations 12-1 through 12-n to the centralized storage location 10. In response to that data, items are typically moved from the central storage location 10 to the decentralized storage locations 12-1 through 12-n or to the remote facility 14 to restock such locations to either replenish dispensed items or to stock new items. Decentralized locations could include satellite pharmacies, computerized medication cabinets, stationary/mobile medication carts, nurse servers, remote hospital pharmacies, supply closets, supply cabinets, etc. Supplies can be reordered from distributors based on levels of stock in the centralized storage location 10.

Figure 2:
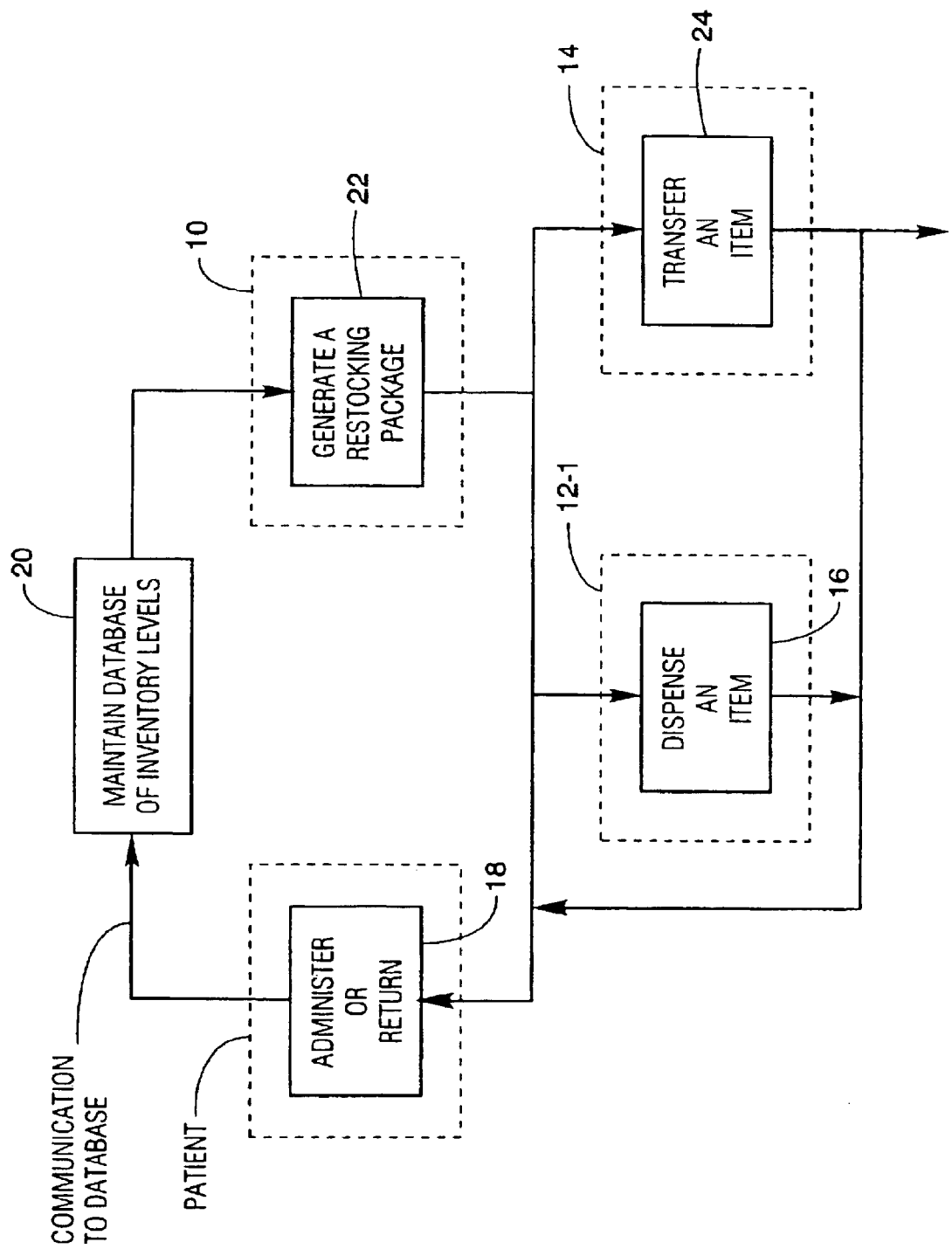
FIG. 2 is a diagram illustrating a process for distributing items and restocking of items based, at least in part, on records created during distribution.

FIG. 2 illustrates a process which may begin with a step of dispensing an item at step of 16 from one of the decentralized storage locations 12-1 to a patient. A dispensing operation may occur in a variety of ways. In a medical facility, dispenses may be completed from medication orders or they may be completed from inventory lists, to name a few types of dispensing operations. Assuming a medication has been dispensed from decentralized storage location 12-1, the medication may either be administered to a patient or returned as shown by step 18. Medications may be returned for a variety of reasons such as the patient has checked out, been moved, or the patient's medication may have been changed. Medications may be returned to the decentralized storage location 12-1. Certain types of medications may simply be replaced in the decentralized storage location 12-1 so as to be used in another dispensing operation, or may need to be disposed of.

The administration of medications occurring at step 18 may be carried out through the use of a hand-held device such as an AcuScan-Rx™ device available from McKesson Automation, Inc., 700 Waterfront Drive, Pittsburgh, Pa. Such devices are wireless devices which communicate with a database to verify the administration of medications to patients. Such communications enable the maintenance of a database of inventory levels as shown by step 20. The database and associated computer system for maintaining the database of inventory levels may be located at the centralized storage location 10 or may be located remote therefrom. In either event, the computer system necessary for maintaining the database provides information which enables the centralized storage location 10 to perform step 22 of generating a restocking package. The generation of the restocking package may be done completely automatically, manually, or through some combination of manual and automatic processes. The restocking package is used to restock the decentralized storage location 12-1.

Restocking packages may also be generated at centralized location 10 and delivered to the remote facility 14. From facility 14 an item may be transferred as shown by step 24. The transfer may be a dispensing step for a patient or a transfer to another location. Items may also be dispensed directly to the patient from the centralized location 10.

Figure 3:
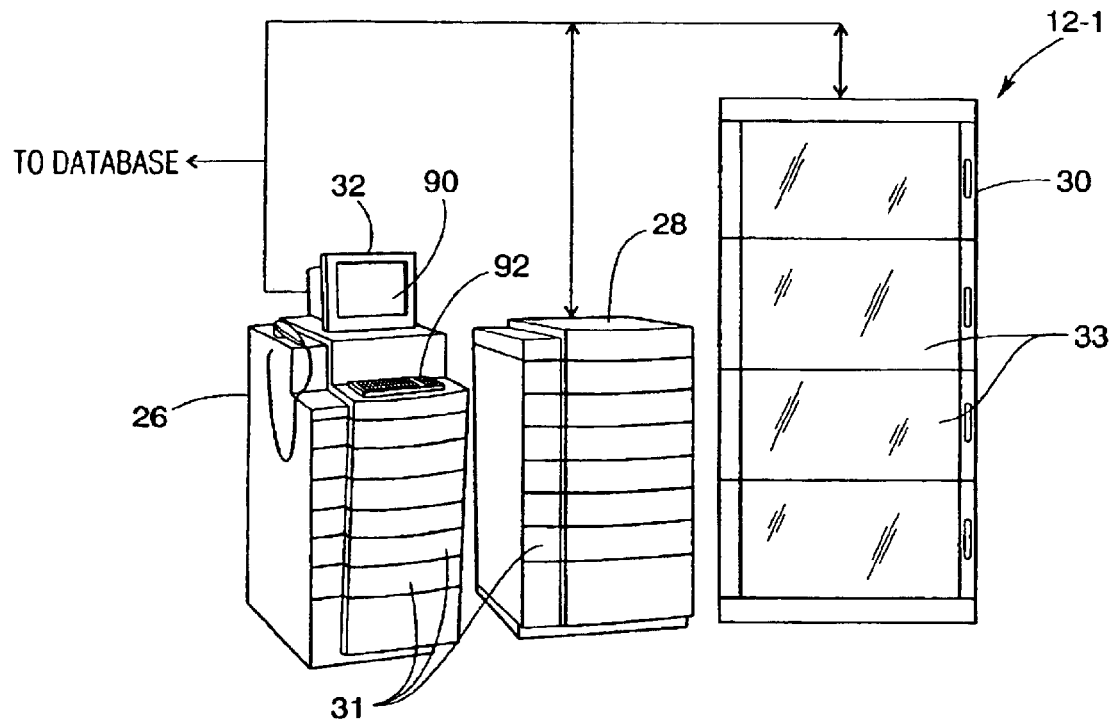
FIG. 3 is one example of hardware located at a decentralized location implementing a closed system for performing dispensing operations.

FIG. 3 illustrates one example of hardware which may be located at any of the decentralized locations 12-1 through 12-n. The hardware illustrated in FIG. 3 is comprised of an AcuDose-Rx™ cabinet 26, having a control computer 32, and an AcuDose-Rx™ auxiliary cabinet 28, available from McKesson Automation, Inc. A supply tower 30 is also illustrated. The control computer 32 controls the operation of the cabinet 26, auxiliary cabinet 28, and supply tower 30. The control computer 32 is also in communication with the central database.

To perform a dispensing operation a user logs onto the control computer 32. After log-on, patient information and information regarding items to be dispensed is entered. Based on the entered information, various drawers 31 in the cabinet 26 and the auxiliary cabinet 28, and various doors 33 on the supply tower 30 are unlocked. After the item to be dispensed has been removed, its removal is recorded at the control computer 32. The user may continue to dispense items for the identified patient, or patient information for another patient may be entered. Entry of information, including log-in, can be performed in a variety of ways with a variety of input devices, e.g., through entry with a keypad, barcode scanning, touch screen, selecting items from a pick list, RF ID, flash memory, magnetic strips, OCR, etc. The reader will understand that the hardware illustrated in FIG. 3 is exemplary and is illustrated for purposes of demonstrating one type of hardware which may be located at the decentralized storage locations 12-1 through 12-n.

The hardware illustrated in FIG. 3 limits access to the items to be dispensed to those individuals who have properly logged on. Thus, the hardware illustrated in FIG. 3 is referred to as a closed system for performing dispensing operations because a dispensing operation cannot be performed unless the user is identified to, and recognized by, the control computer 32.

Figure 4:
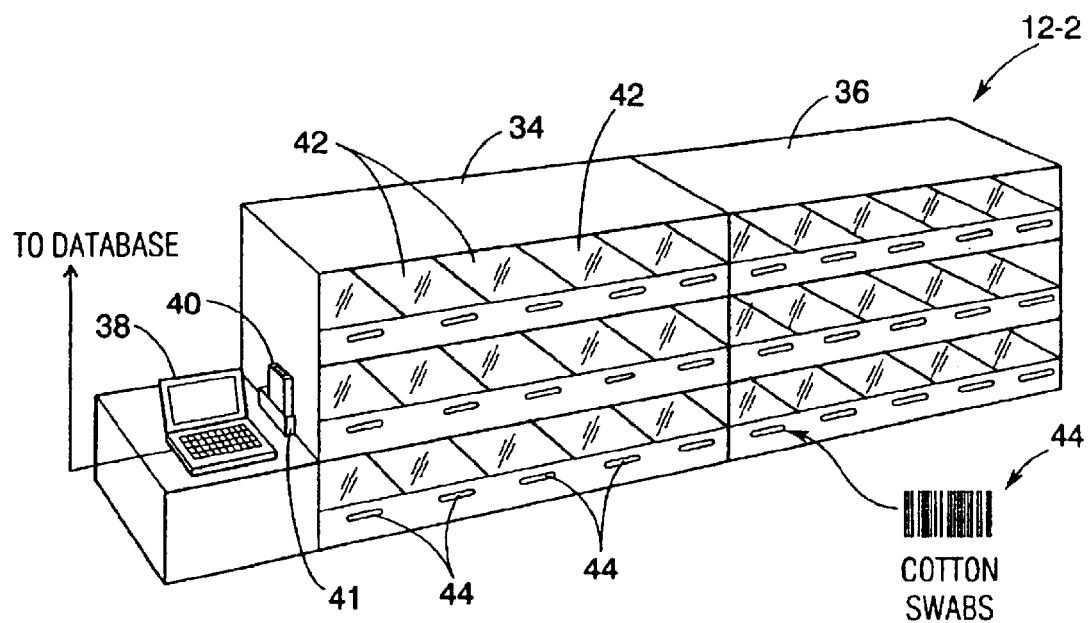
FIG. 4 is one example of hardware located at a decentralized location implementing an open system for performing dispensing operations.

FIG. 4 illustrates another example of hardware which may be located at any of the decentralized storage locations 12-1 through 12-n. The hardware is comprised of a first shelving unit 34 and a second shelving unit 36. An optional interface computer 38 may be provided, which is in communication with the database. If the interface computer is 38 is not provided, a handheld device 40 can be carried into the area to perform the inventory of the shelves. The handheld device 40 is taken back to the centralized storage location 10 where the information is downloaded in any appropriate manner. Alternatively, the hand-held device 40 could be a wireless device communicating over a wireless network link. Alternatively, and as shown in FIG. 4, the hand-held device 40 may be located in the area and have a docking cradle 41 in communication with the interface computer 38.

Each of the shelving units 34, 36 is comprised of a plurality of bins 42. Each of the bins carries indicia 44 which may be, for example, a barcode and/or a label identifying the contents of the bin. Additionally, items in the bins may have a bar code, label or other indicia directly on them or on their packaging. The bar code could be scanned, or other methods of inputting the data consistent with the type of indicia used, or push buttons or the like actuated, to perform a dispensing or other type of operation. In addition, the handheld device 40 could be used to generate an ad hoc order through its screen entry in the event that an item is not available to be scanned or otherwise have data pertinent thereto input. The number of shelving units 34, 36 and the configuration of the bins 42, depends upon the number and size of the items to be stocked. Because access to the bins 42 is not restricted, the hardware illustrated in FIG. 4 is referred to as an open system for performing dispensing operations. The reader will understand that the hardware illustrated in FIG. 4 is exemplary and is illustrated for purposes of demonstrating one type of hardware which may be located at the decentralized storage locations 12-1 through 12-n.

Figure 5:
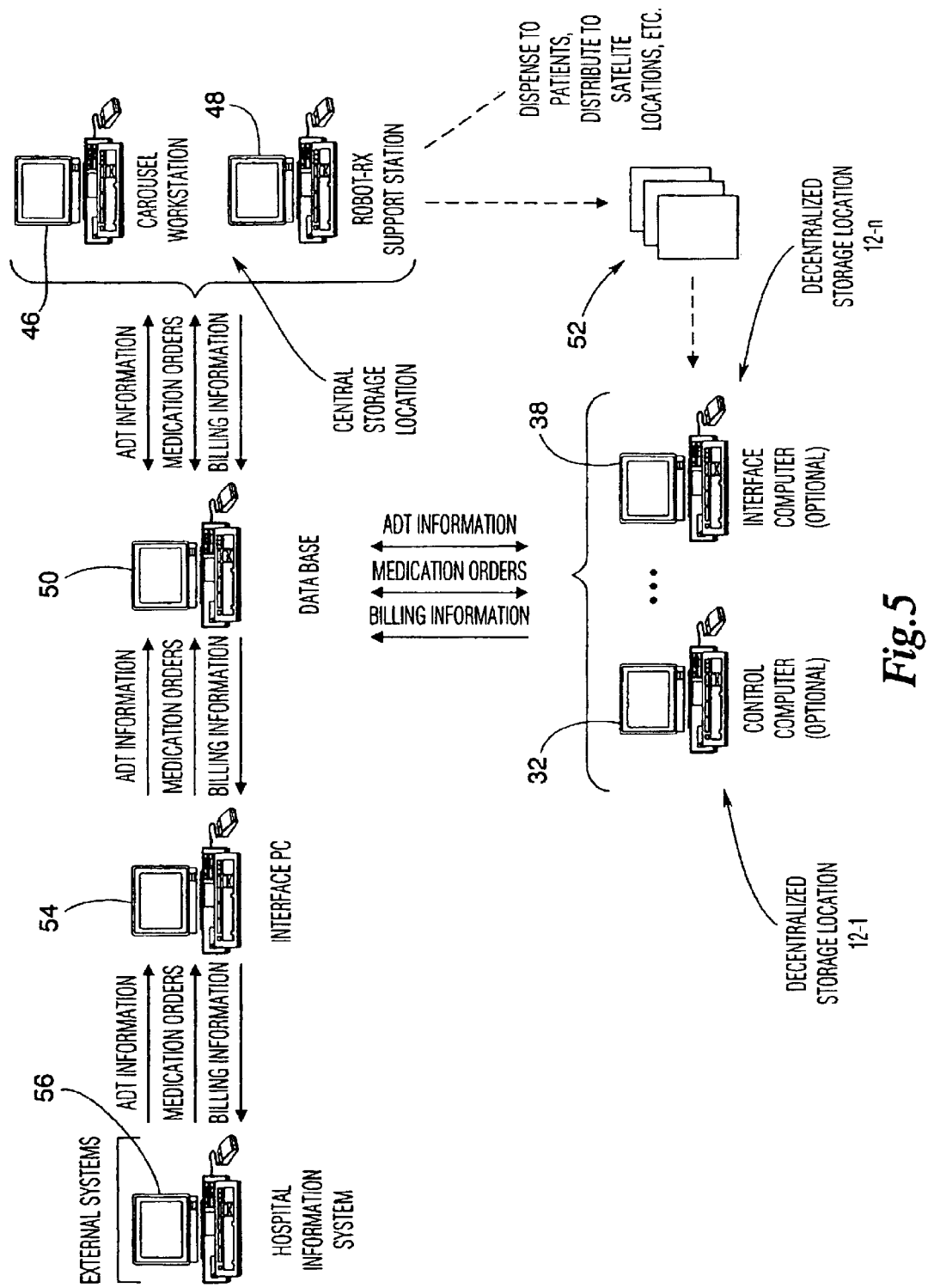
FIG. 5 is a diagram illustrating the flow of information between the computers used at various locations within a dispensing/restocking system.

FIG. 5 illustrates the computers used at various locations within a dispensing/restocking system of the type disclosed herein. As seen in FIG. 5, decentralized storage location 12-1 is where control computer 32 (if supplied) is located. Decentralized storage location 12-n is where interface computer 38 (if supplied) is located. A carousel work station 46 is located at the centralized storage location 10. The centralized storage location 10 may also have a Robot-Rx™ support station 48 which is used to control a robot.

A computer 50, which may be located at centralized storage location 10 or may be located elsewhere, maintains the database for the system. The computer 50 receives information from the decentralized storage locations 12-1 through 12-n and provides information to the carousel work station 46 and/or the Robot-Rx™ support station 48 to enable restocking packages 52 to be prepared. Additionally, dispenses to patients, distributions to satellite facilities, and the like may occur from centralized location 10. An interface PC 54 may be provided to enable external systems, such as a PC 56 on which a hospital information system resides, to communicate with the computer 50 on which the database is located. Completing the description of FIG. 5, as has been previously described, restocking packages 52 are prepared at the centralized storage location 10 and delivered to the decentralized storage locations 12-1 through 12-n.

Returning to FIG. 3, the cabinet 26 available from McKesson Automation, Inc. may be configured with eight (8) drawers and has a maximum capacity of 384 line items. The control computer 32 operates in conjunction with a color touch screen monitor 90 and a full sized keyboard 92. An integral uninterrupted power supply (not shown) is provided. A scanner port may also be provided to attach a bar code scanner.

The auxiliary cabinet 28 available from McKesson Automation, Inc. attaches to the main cabinet 26 to expand storage space of narcotic, floor stock and PRN medications. Like the cabinet 26, the cabinet 28 may be configured with eight (8) drawers and has a maximum capacity of 384 line items.

Figure 6:
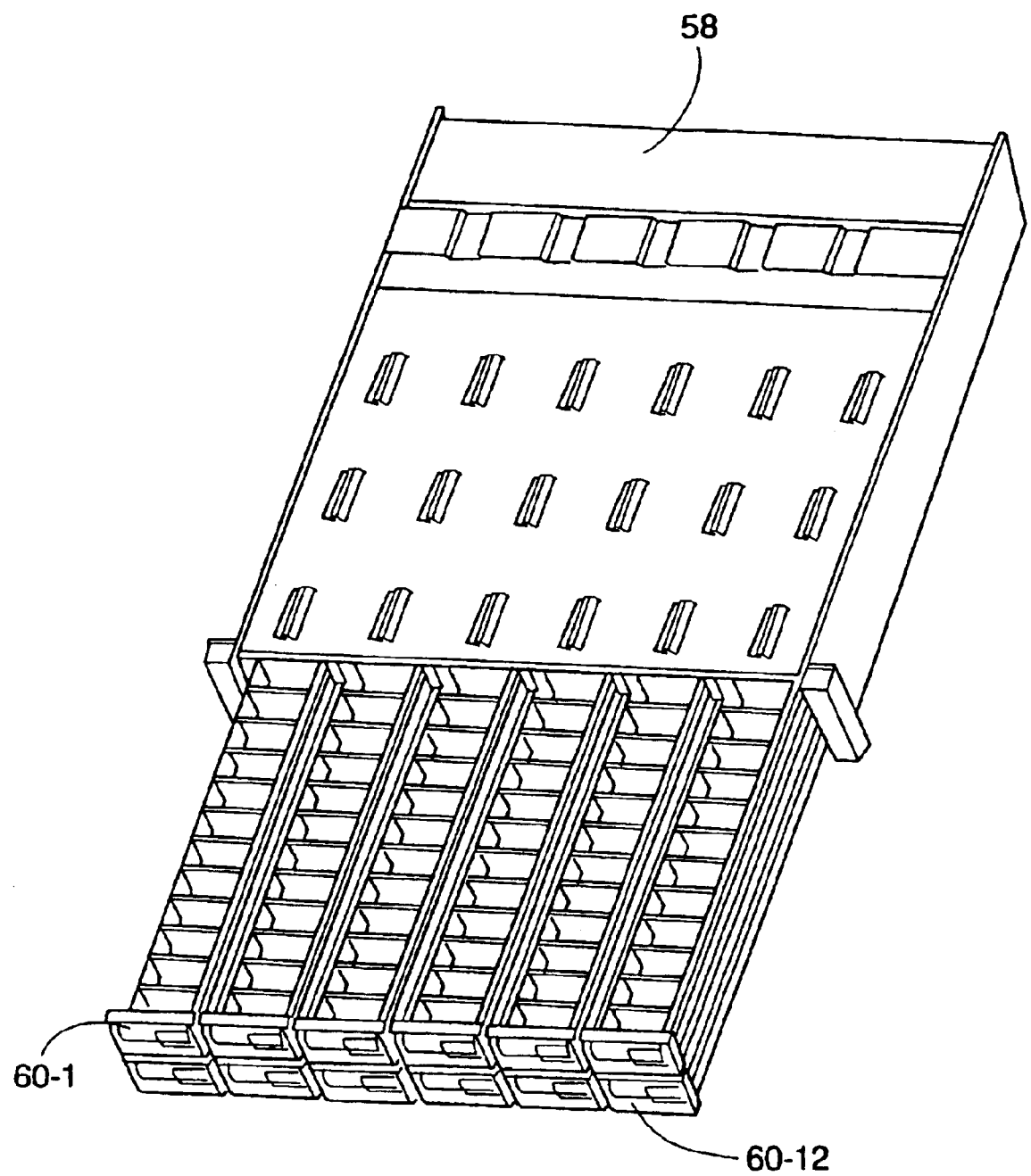
FIG. 6 illustrates a unit dose drawer that may be used in the cabinet or the auxiliary cabinet of FIG. 3.
Figure 7:
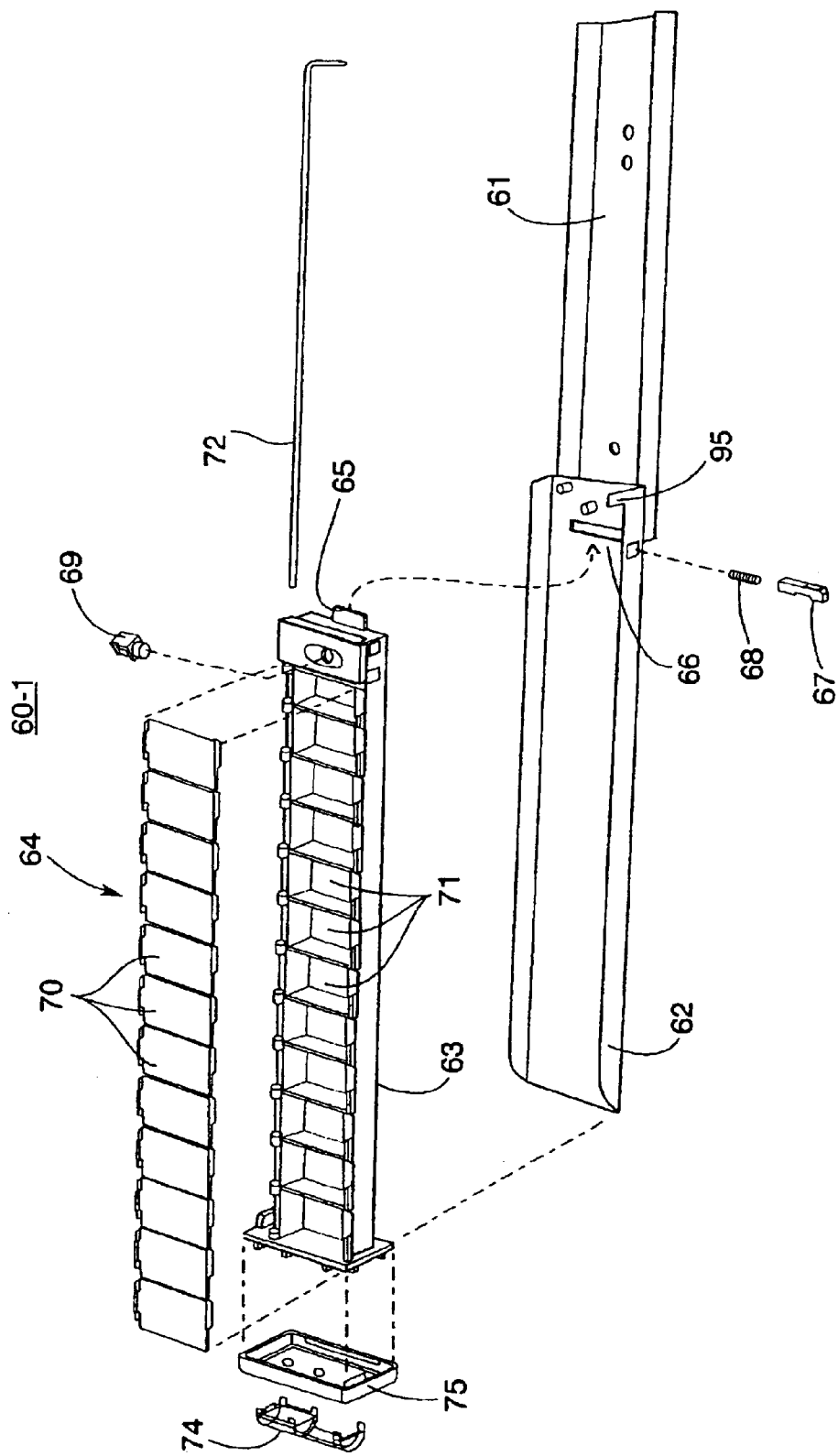
FIG. 7 is an exploded view of one example of the construction of an individual drawer of the type shown in FIG. 6.

A unit dose dispensing drawer 58 is illustrated in FIG. 6. As the name implies, the unit dose dispensing drawer 58 provides single unit-of-use access to high security medications that are to be stored within either the cabinet 26 or auxiliary cabinet 28, although access to more than a single unit could be provided if the user so desired. The unit dose dispensing drawer 58 uses one standard drawer space within the cabinets 26, 28. The unit dose dispensing drawer 58 may be provided with twelve (12) individual drawers 60-1 through 60-12 or in a wider six-drawer version (not shown). Each of the individual drawers 60-1 through 60-12 is motor-driven so as to provide access to exactly the number of units requested. The construction of the individual drawers 60-1 through 60-12 is shown in FIG. 7.

Each of the drawers 60-1 through 60-12 is comprised, in the presently preferred embodiment, of a drivable tray 62 which moves relative to a slide 61, an insert 63 and a lid 64. The drivable tray 62 is connected to a chain, described herein below, so as to be driven between an open position shown in FIG. 7 and a closed position.

The insert 63 has a tab 65 which mates with a slot 66 in the tray 62. The insert is approximately the size of the tray 62 such that the insert 62 defines the volume of the drawer 60-1. A pin 67 and spring 68 are inserted through an opening in the side of the tray 62 and retained within insert 63 by a pushbutton 69. Upon depressing the pushbutton 69, the spring 68 pushes pin 67 out of its locked position thereby enabling the insert 63 to be removed from the tray 62. The pin 67, spring 68, and pushbutton 69 form a release mechanism. The insert 63 can only be removed from the tray 62 if the tray 62 is driven to its fullest extent. Access to the command to drive the tray 62 to its fullest extent can be password protected so that only administrators and/or pharmacy techs have access.

The unit dose dispensing drawer of the present invention will also support a feature called "auto ID." This feature incorporates a chip, switch, or other mechanism for generating, for example, an eight bit signal. The control computer's 32 software automatically detects the eight bit signal and determines from a table the hardware configuration of any drawer type that is installed in the cabinet. Eight bits enables 256 possible drawer types and configurations using this feature. This feature could also be used on standard drawers used in the cabinets. Additionally, the drawers can be bar-coded to provide data about the drawers.

The lid 64 is comprised of a plurality of individual lids 70 which are designed to cover individual compartments 71. The lid 64 is held in place with respect to the insert 63 by a rod 72. As seen in FIG. 7, the hinge between each individual lid 70 and each individual compartment 71 is along the side of the insert 63. Accordingly, the individual lid 70 can be fully opened only when the tray 62 is driven so that the individual lid 70 is completely clear of the front portion of the cabinet. The lid 64 can be locked, or can be provided with a tamper-resistant seal, to prevent access when the insert 63 is removed from the tray 62. That capability can be used to centrally restock the cabinet as inserts 63 are swapped and refilled in the pharmacy or other central storage location. Thus the inserts 63 may provide the function of the restocking packages 52 of FIG. 5.

The drawer 60-1 is completed by a fascia piece 74 and a knob 75. The end of the tray 62 may have slots and/or tabs which mate with slots and/or tabs at the corresponding end of insert 63.

Those of ordinary skill in the art will recognize that other types of inserts 63, other configurations for providing locked lids, other configurations for releasing the insert from the tray, and other fascia and knob configurations are possible. FIG. 7 is provided only for the purpose of illustrating a presently preferred embodiment. Those of ordinary skill in the art will recognize that many modifications and variations are possible.

Figure 9:
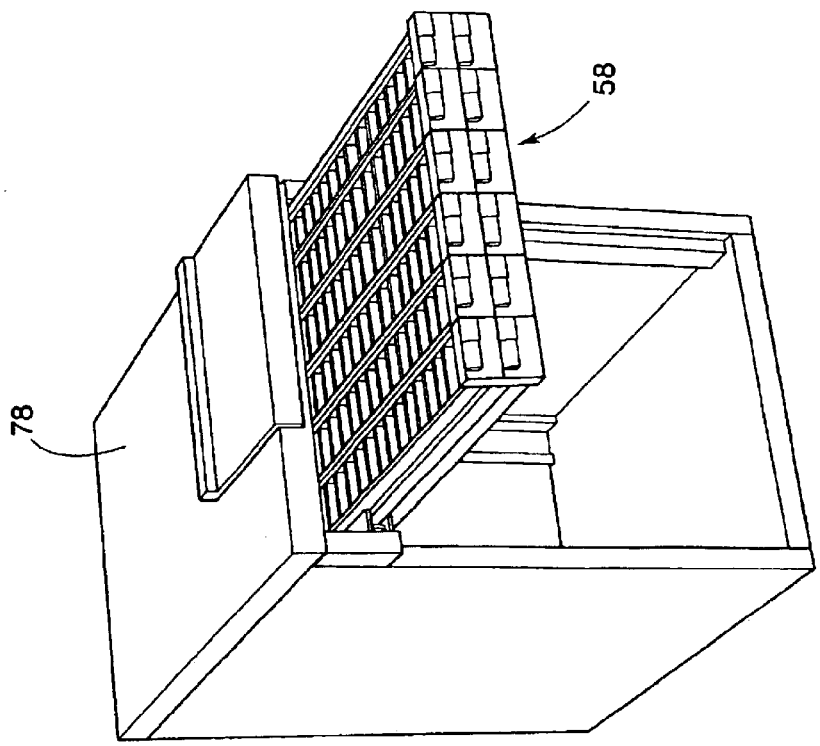
FIG. 9 illustrates the unit dose drawer in a fully opened condition in a cabinet without any other drawers.
Figure 8:
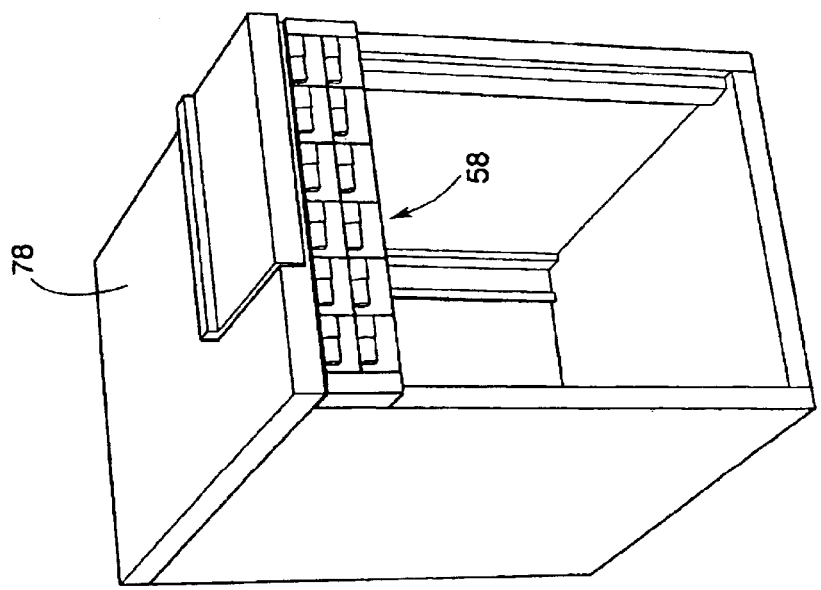
FIG. 8 illustrates the unit dose drawer in a fully closed position in a cabinet without any other drawers.

FIG. 8 illustrates the unit dose drawer 58 of FIG. 6 in a fully closed position in a cabinet 78 without any other drawers. FIG. 9 illustrates the unit dose drawer 58 of FIG. 6 in a fully opened position in the cabinet 78.

Figure 10:
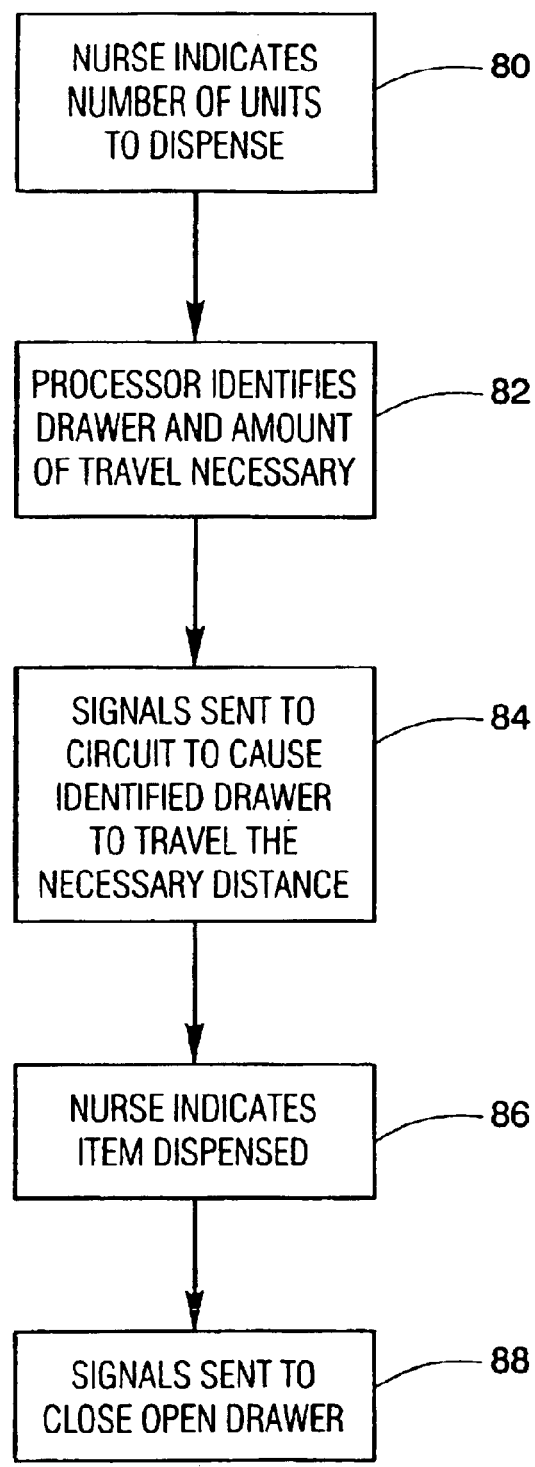
FIG. 10 is a flow chart illustrating a dispense operation from a unit dose drawer.

FIG. 10 is a flow chart illustrating a dispense operation from a unit dose drawer. Assuming that the nurse has properly logged into the cabinet and identified a patient, the dispense operation from the unit dose drawer begins at step 80 in which the nurse indicates the number of units of a medication, previously identified, to be dispensed. At step 82, the control computer 32 identifies the drawer containing the desired medication and the amount of travel necessary to make the next pocket or pockets containing the medication accessible. At step 84, signals are sent to a circuit which causes the identified drawer to travel the necessary distance thereby providing access to the necessary pocket or pockets. The nurse then removes the medication from the accessed pockets and provides an indication that the items have been dispensed at step 86. The control computer 32, upon receiving an indication that a dispense has occurred, at step 88 sends signals which identify the open drawer and cause the drawer to be driven to its closed position. The foregoing process may be used for one unit-dose of medication where the same medication is in all pockets or can be used for multiple units of the same medication where the same medication is in all pockets. In a situation where multiple units of the same medication are to be dispensed, but different medications are in the drawer pockets, the nurse indicates the number of units to dispense. The drawer then fully extends exposing all of the pockets. The nurse dispenses the desired medications from the fully opened drawer. Such a "matrix mode" of dispensing would be used only in connection with noncontrolled substances.

Figure 11:
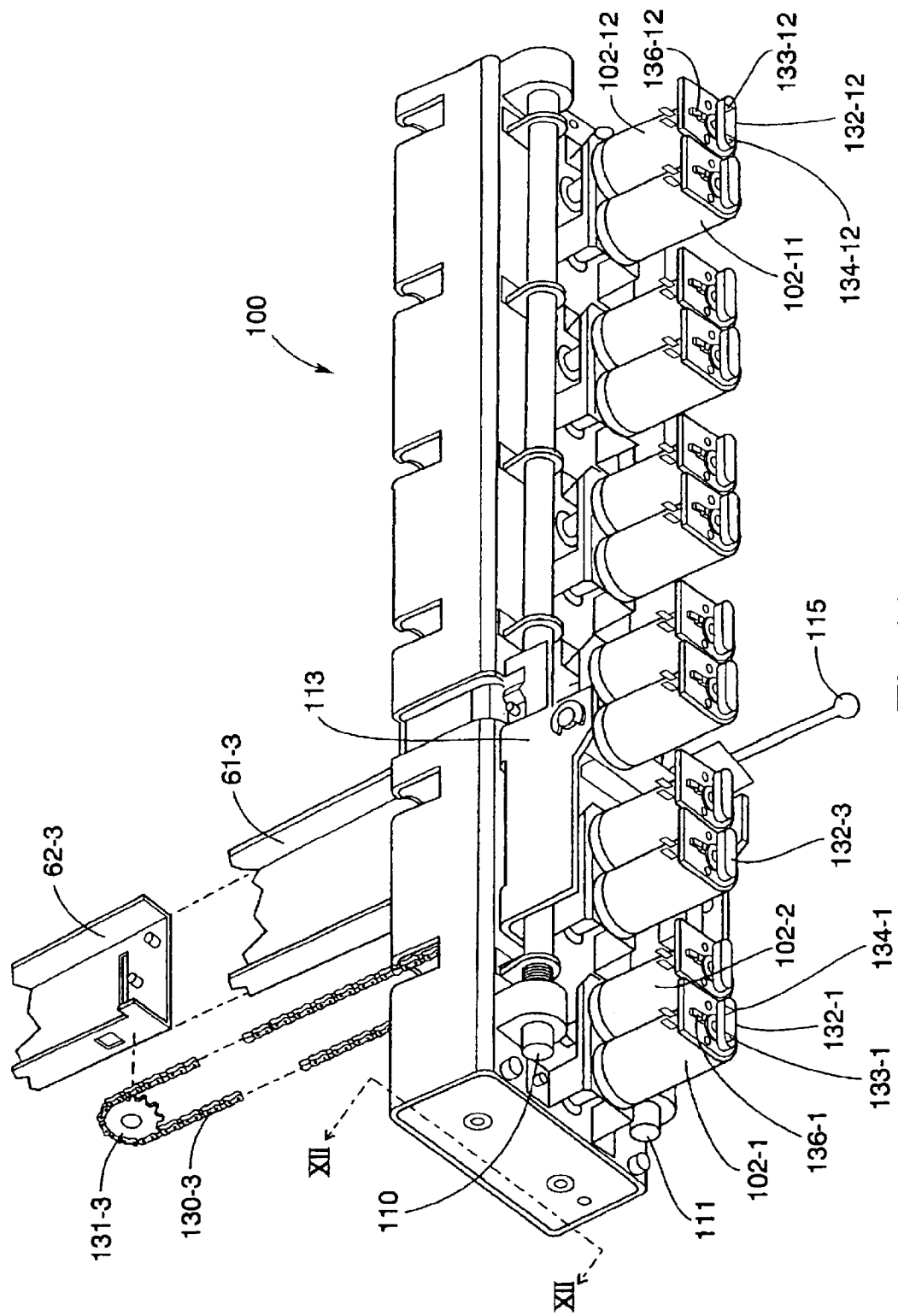
FIG. 11 is a perspective view of a drive chassis located at the rear of a unit dose drawer having twelve drawers.
Figure 12:
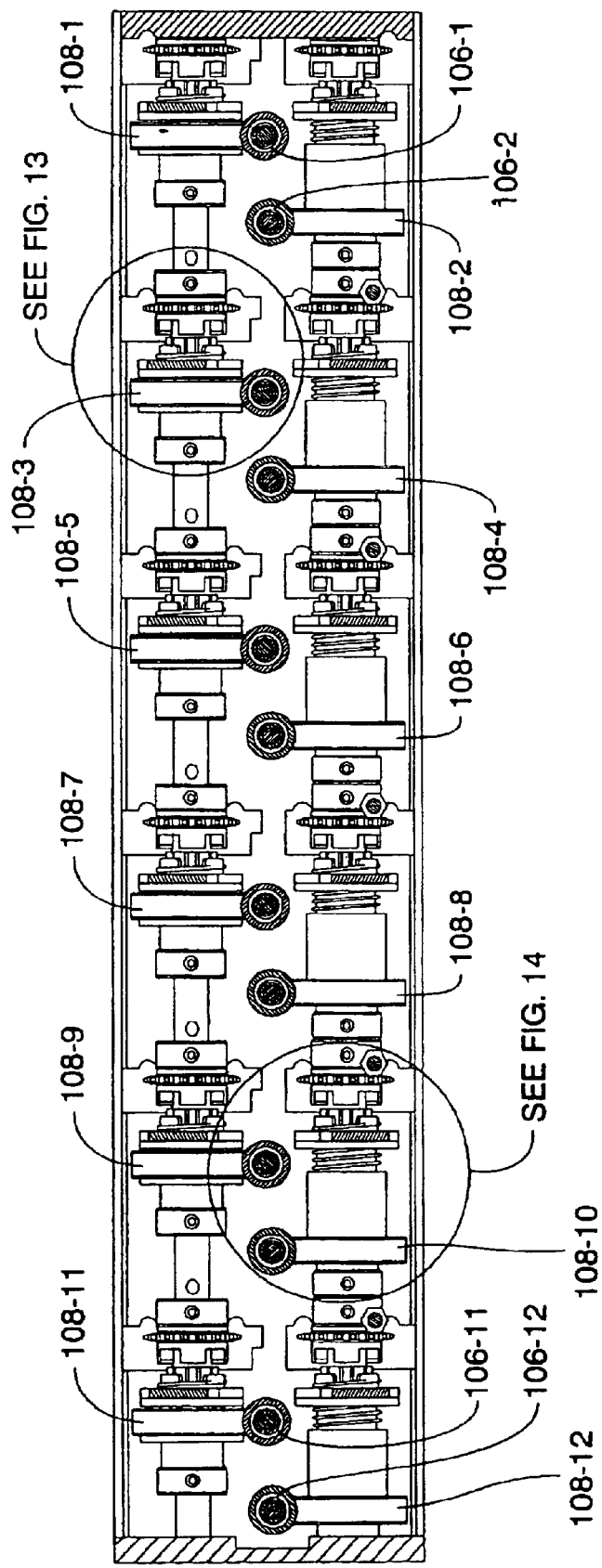
FIG. 12 is a cross-section view taken along the lines XI—XI in FIG. 11.

The mechanical hardware for driving the trays 62 is illustrated in FIGS. 11 through 15. In FIG. 11, a perspective view of a drive chassis 100 is illustrated. The chassis carries motors 102-1 through 102-12 which are each used to drive one tray 62. As seen best in FIG. 15, a shaft 104-1 through 104-12 of each motor drives an associated worm gear 106-1 through 106-12, respectively. As seen best in FIGS. 12 and 15, each side-by-side pair of motors drives one of the upper trays and the lower tray directly beneath it. That is accomplished, in part, by each worm gear 106-1 through 106-12 mating with and driving a gear 108-1 through 108-12. An upper clutch rod 110 carries odd numbered gears 108-1, 108-3, 108-5, 108-7, 108-9, and 108-11 while a lower clutch rod 111 carries even numbered gears 108-2, 108-4, 108-6, 108-8, 108-10, and 108-12. The upper clutch rod 110 and lower clutch rod 111 are responsive to an override mechanism 113 operated by a user through an override bar 115. Movement of the override bar 115 to the right in FIG. 11 causes both the upper clutch rod 110 and lower clutch rod 111 to move to the left as seen in FIG. 11. As will now be described, lateral displacement of the upper clutch rod 110 and lower clutch rod 111 disengages the trays from the motors.

Figure 13:
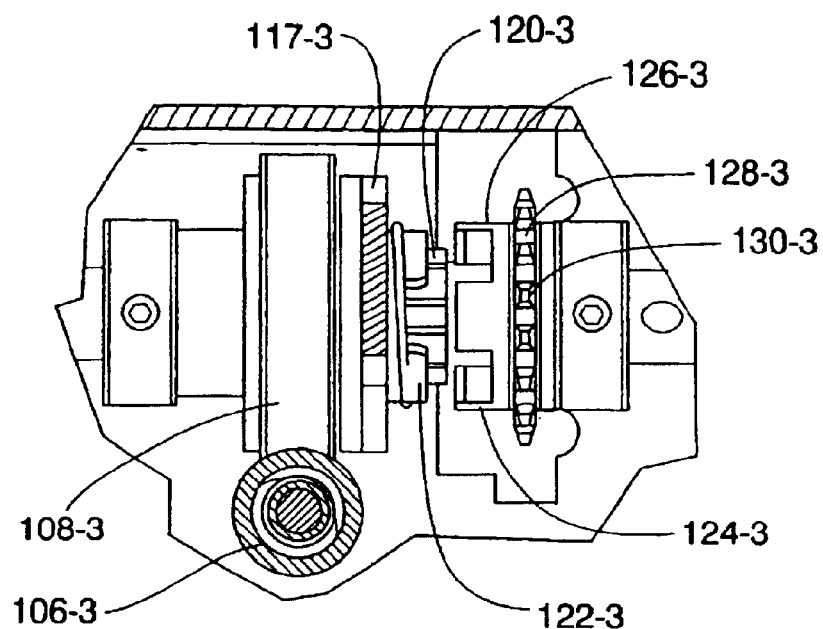
FIGS. 13 and 14 illustrate details of portions of FIG. 12.
Figure 14:
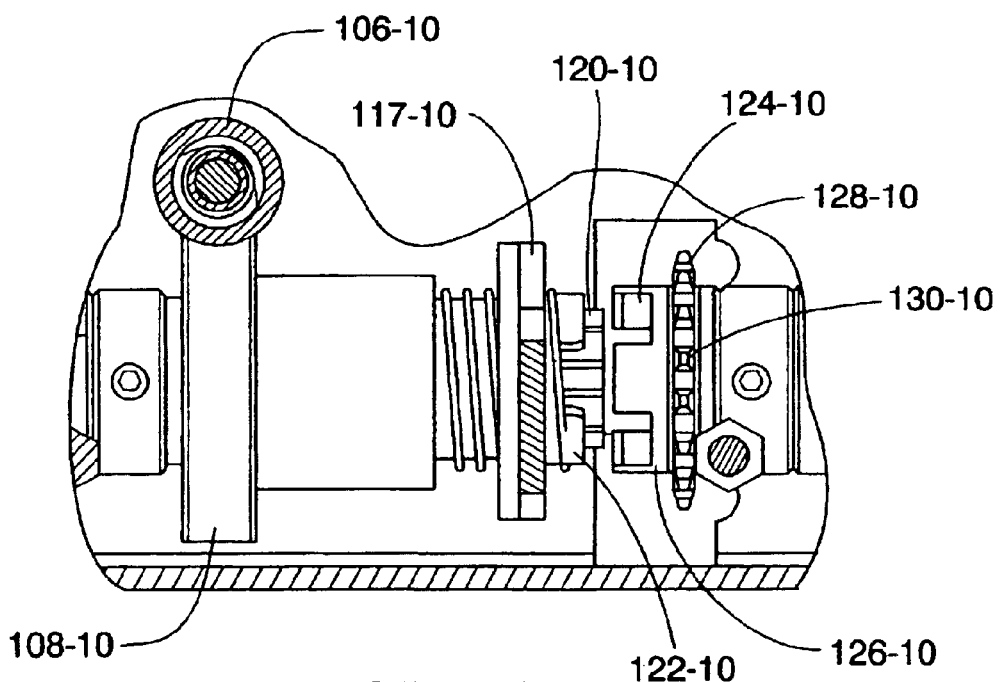
Figure 15:
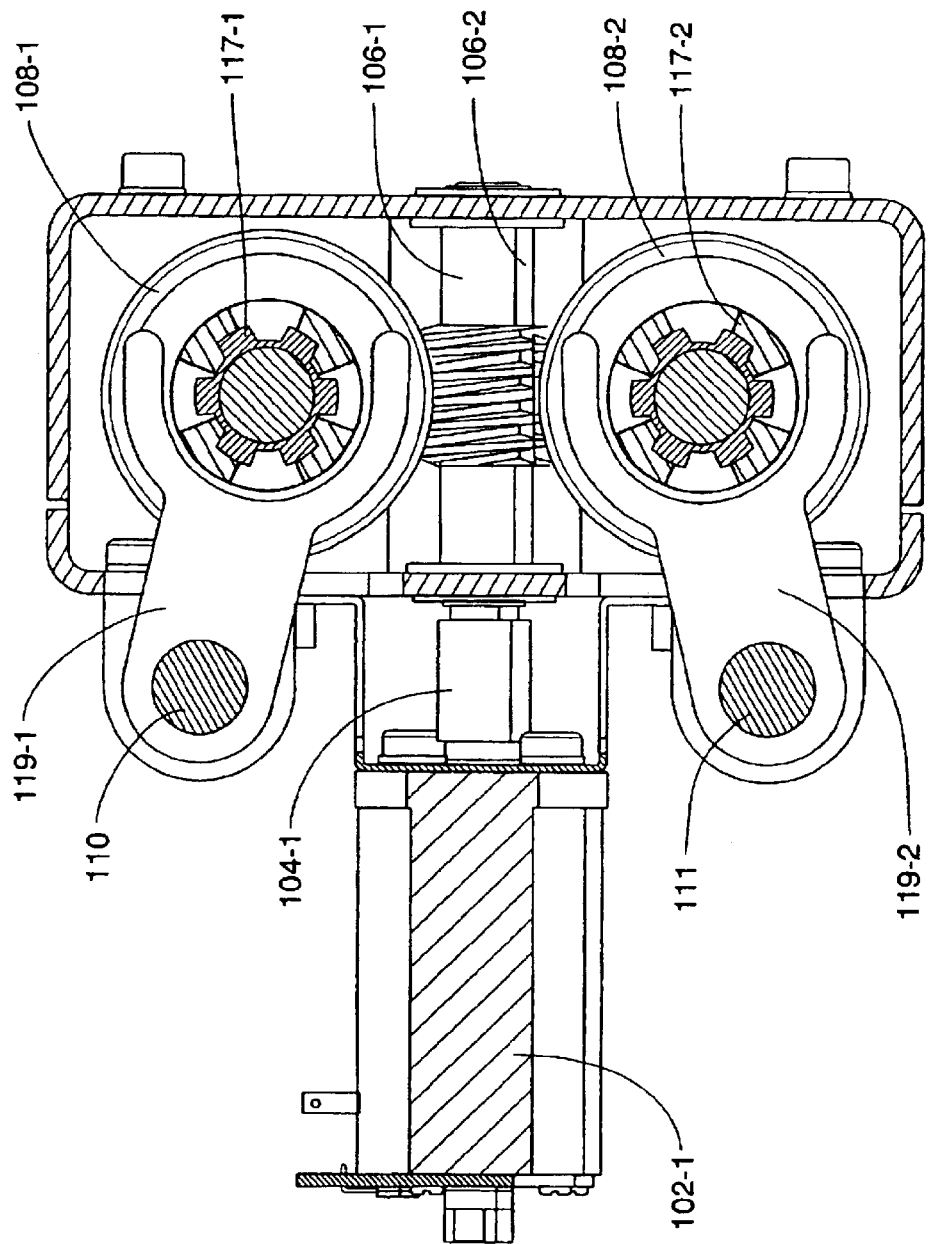
FIG. 15 illustrates the details of the worm drive.

Each of the gears 108-1 through 108-12 has associated therewith a moveable gear 117-1 through 117-12, respectively, seen best in FIGS. 13, 14, and 15. The moveable gears 117-1 through 117-12 are free to move along their respective clutch rods 110, 111 while at all times being drivable by their associated gear 108-1 through 108-12, respectively. That may be accomplished, as seen in FIGS. 13 and 14, by providing gears 108-1 through 108-12 with a hub 120-1 through 120-12 having a flattened or shaped exterior circumference which mates with a similarly shaped interior circumference of the moveable gears 117-1 through 117-12, respectively.

Each of the moveable gears 117-1 through 117-12 has associated therewith a clutch fork 119-1 through 119-12, respectively, best seen in FIG. 15. Each of the clutch forks 119-1 through 119-12 is connected to one of the clutch rods 110, 111. As seen in FIGS. 13 and 14, teeth 122-1 through 122-12 of moveable gears 117-1 through 117-12 are adapted to engage teeth 124-1 through 124-12 of a driven gear 126-1 through 126-12, respectively. Each of the driven gears 126-1 through 126-12 has a set of teeth 128-1 through 128-12, respectively, along its outer periphery.

During normal operation, the clutch rods 110, 111 are biased so that the teeth 122-1 through 122-12 of moveable gears 117-1 through 117-12 mate with the teeth 124-1 through 124-12 of driven gear 126-1 through 126-12, respectively. When the override bar 115 is moved to the right in FIG. 11, the clutch rods 110 and 111 overcome the bias, normally provided by springs, and therefore move to the left as seen in FIG. 11. Movement to the left of the clutch rods 10, 111 causes each of the clutch forks 119-1 through 119-12 to move to the left pushing with it the moveable gears 117-1 through 117-12, respectively. Movement of the moveable gears 117-1 through 117-12 to the left, causes the teeth 122-1 through 122-12 of the moveable gears 117-1 through 117-12 to disengage from the teeth 124-1 through 124-12 of driven gear 126-1 through 126-12, respectively. When that occurs, driven gears 126-1 through 126-12 are no longer connected via the worm drive to the electric motors 102-1 through 102-12.

A chain 130-1 through 130-12 engages the teeth 128-1 through 128-12 of driven gear 126-1 through 126-12, respectively. The other end of the chain may engage an idler gear, one of which 131-3 is shown in FIG. 11. Each chain is connected to one of the trays so that the tray moves with the chain. In FIG. 11, chain 130-3 is connected to tray 62-3. During normal operation, when any of the motors 102-1 through 102-12 is energized, its shaft rotates thereby rotating the worm gear 106-1 through 106-12 and associated gears 108-1 through 108-12, which in turn rotates its associated moveable gear 117-1 through 117-12, which drives the driven gear 126-1 through 126-12 causing the chain 130-1 through 130-12 to move, respectively. Because each tray is attached to its own chain, the position of the tray can be controlled by controlling the amount of rotation of each motor's shaft The worm gear is designed to be self locking. More specifically, when the motor is not energized, the worm gear is designed so that there is sufficient friction to prevent the tray from moving, and hence preventing the drawer from being opened or closed. In the event of a power failure, control computer 32 malfunction, or other event which creates a state in which the drawers cannot be driven by the motors to their open position, the override bar may be used as previously described to disengage the moveable gears from the driven gears. When that occurs, the drawers are no longer connected to the worm gear such that the driven gears 126-1 through 126-12 are free to rotate thereby allowing each of the drawers to be opened and closed.

Returning to FIG. 11, each of the motor shafts 104-1 through 104-12 carries a sensor blade 132-1 through 132-12, respectively. The sensor blades 132-1 through 132-12 each carry two magnets 133-1 through 133-12 and 134-1 through 134-12, respectively. Each of the motors 102-1 through 102-12 is provided with a Hall effect sensor 136-1 through 136-12, respectively. Thus, as the sensor blade 132-1 through 132-12 rotates its magnets 133-1 through 133-12, 134-1 through 134-12, the magnets are brought adjacent to the Hall effect sensor 136-1 through 136-12, respectively, such that a 360° rotation of the motor shaft produces two pulses. Those pulses are input to control electronics which will now be described in conjunction with FIGS. 16 through 29.

Figure 16:
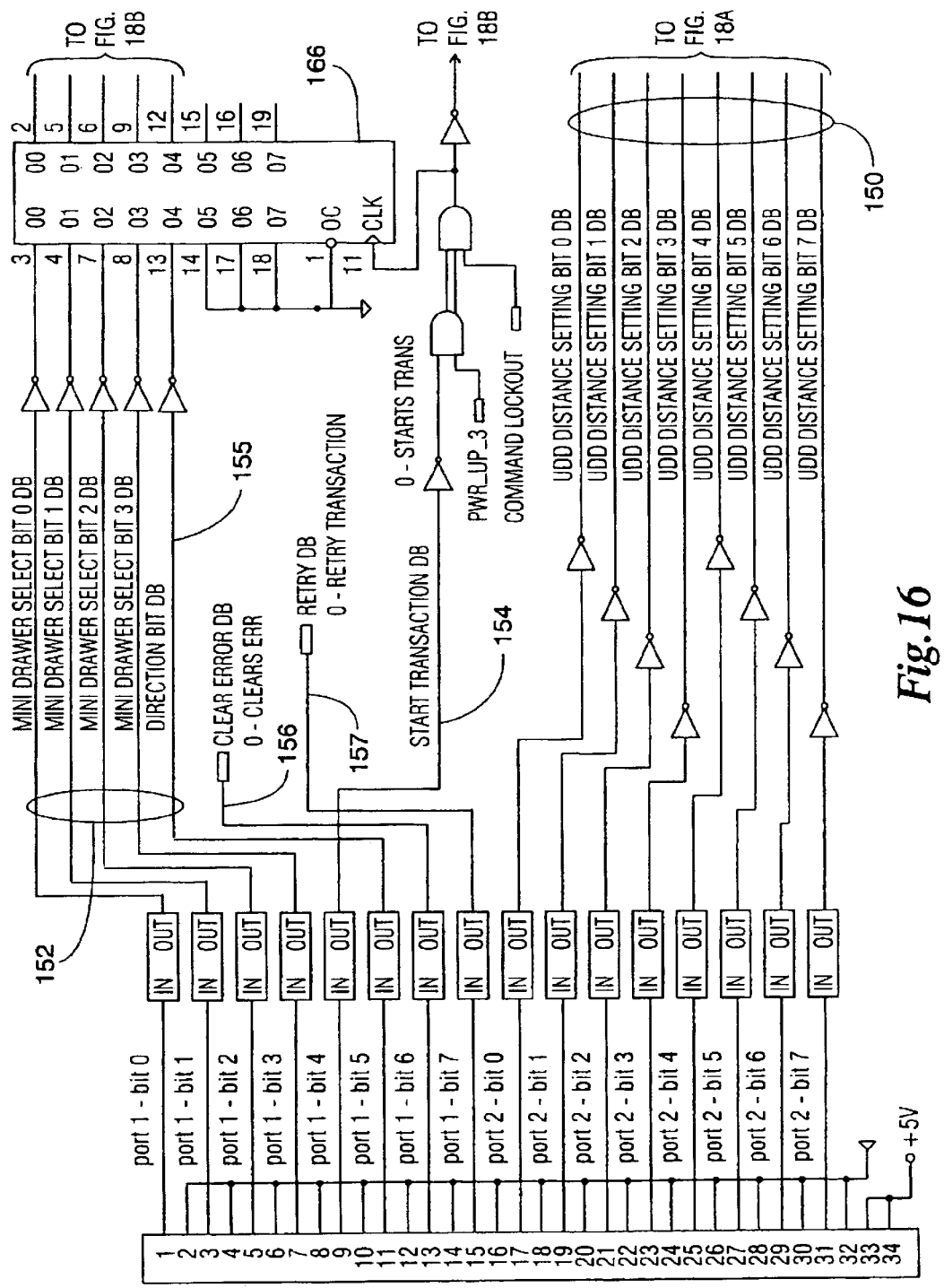
FIGS. 16–20 are electrical schematics of a circuit for receiving drawer identification and distance information as well as certain feedback signals which are used by the circuit to generate certain control signals.
Figure 17A:
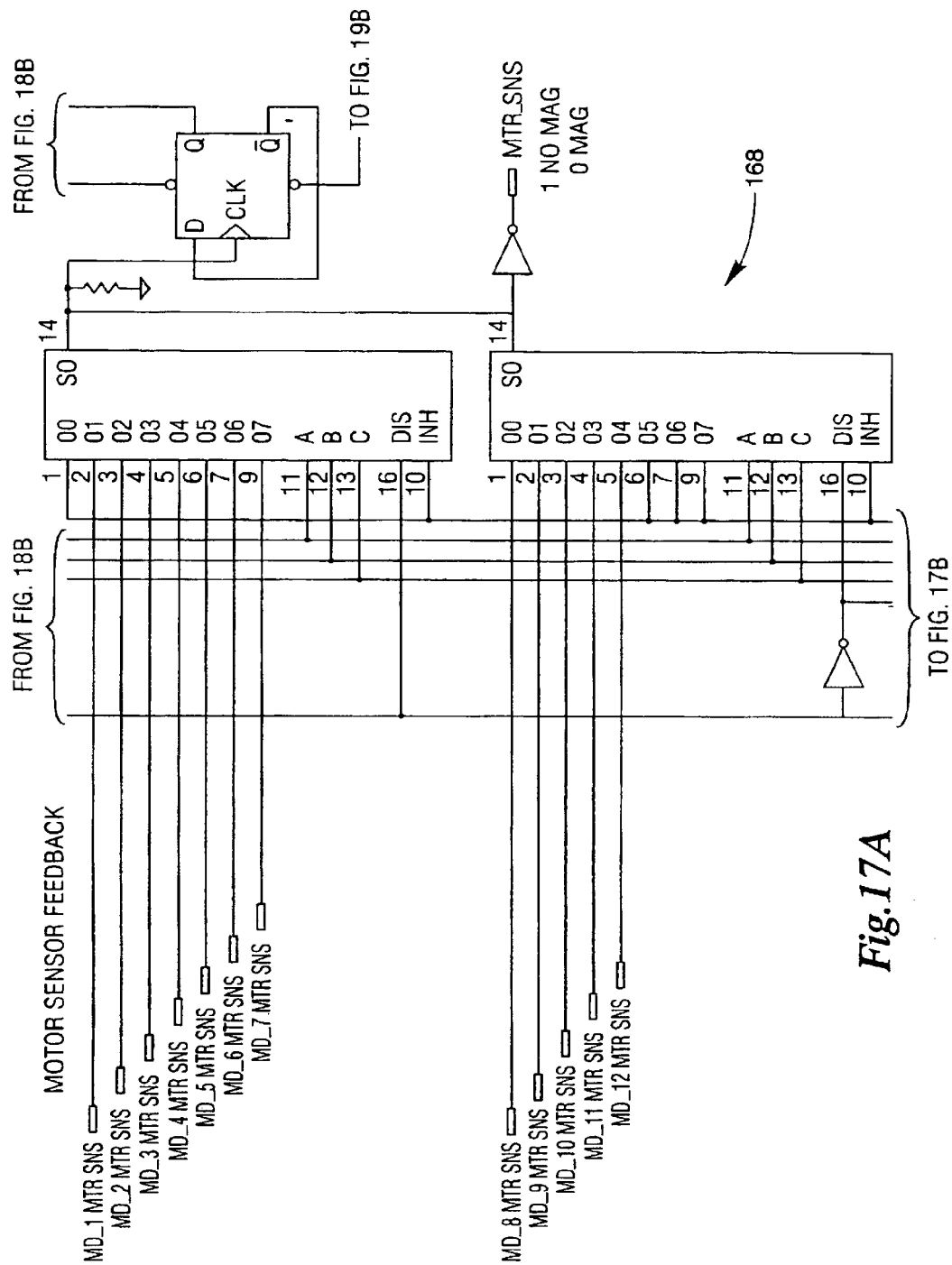
Figure 17B:
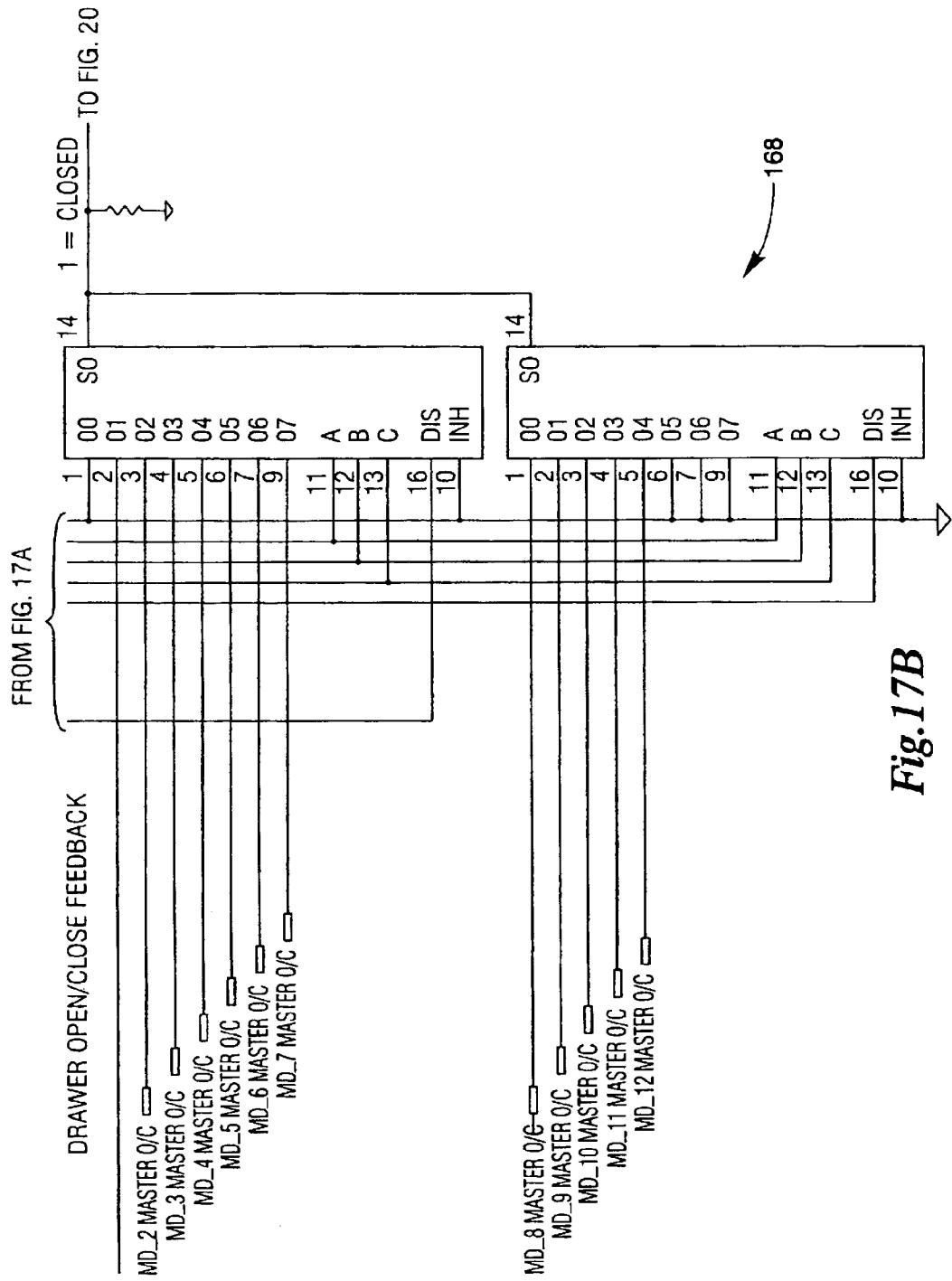
Figure 18A:
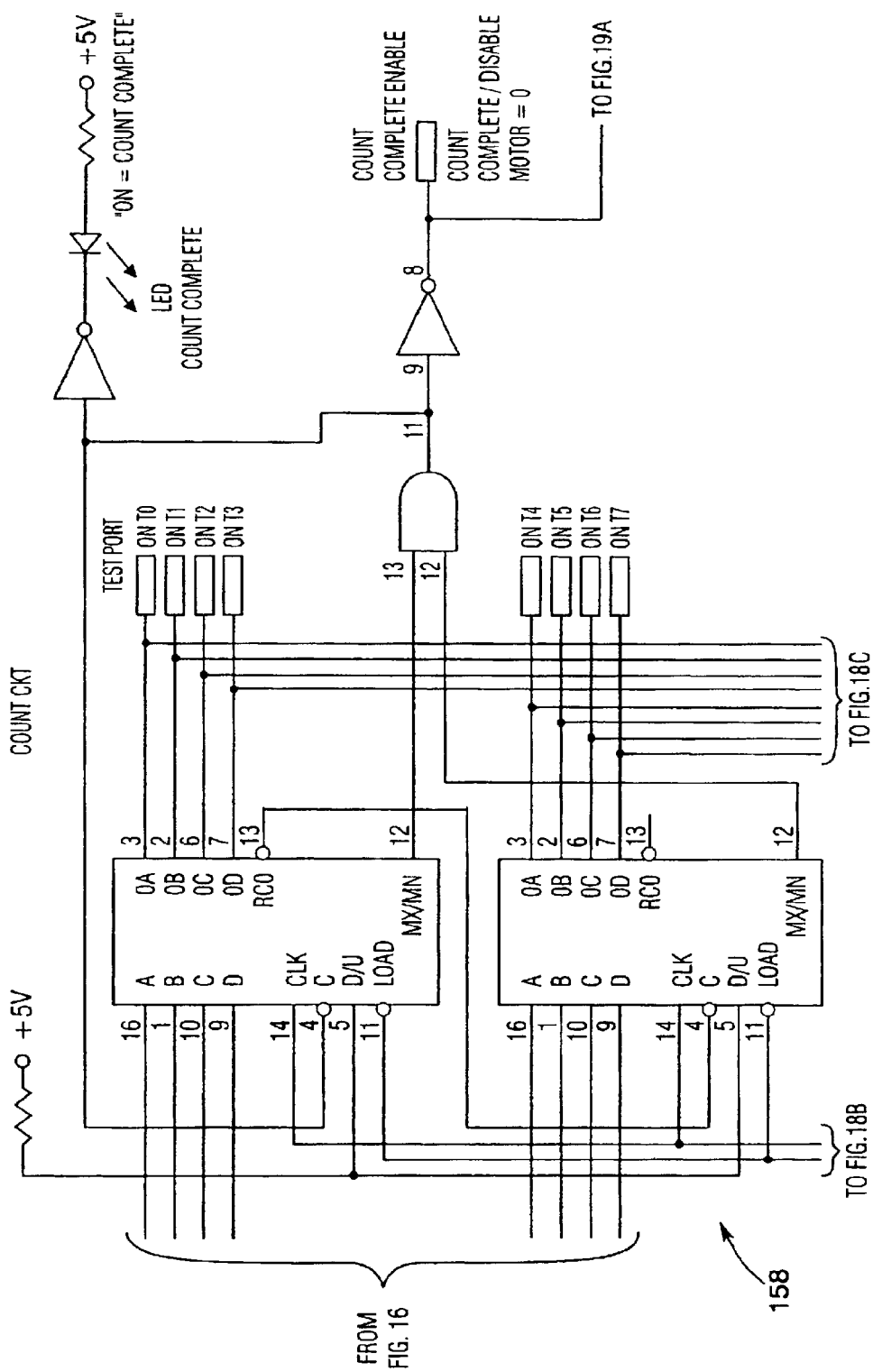
Figure 18B:
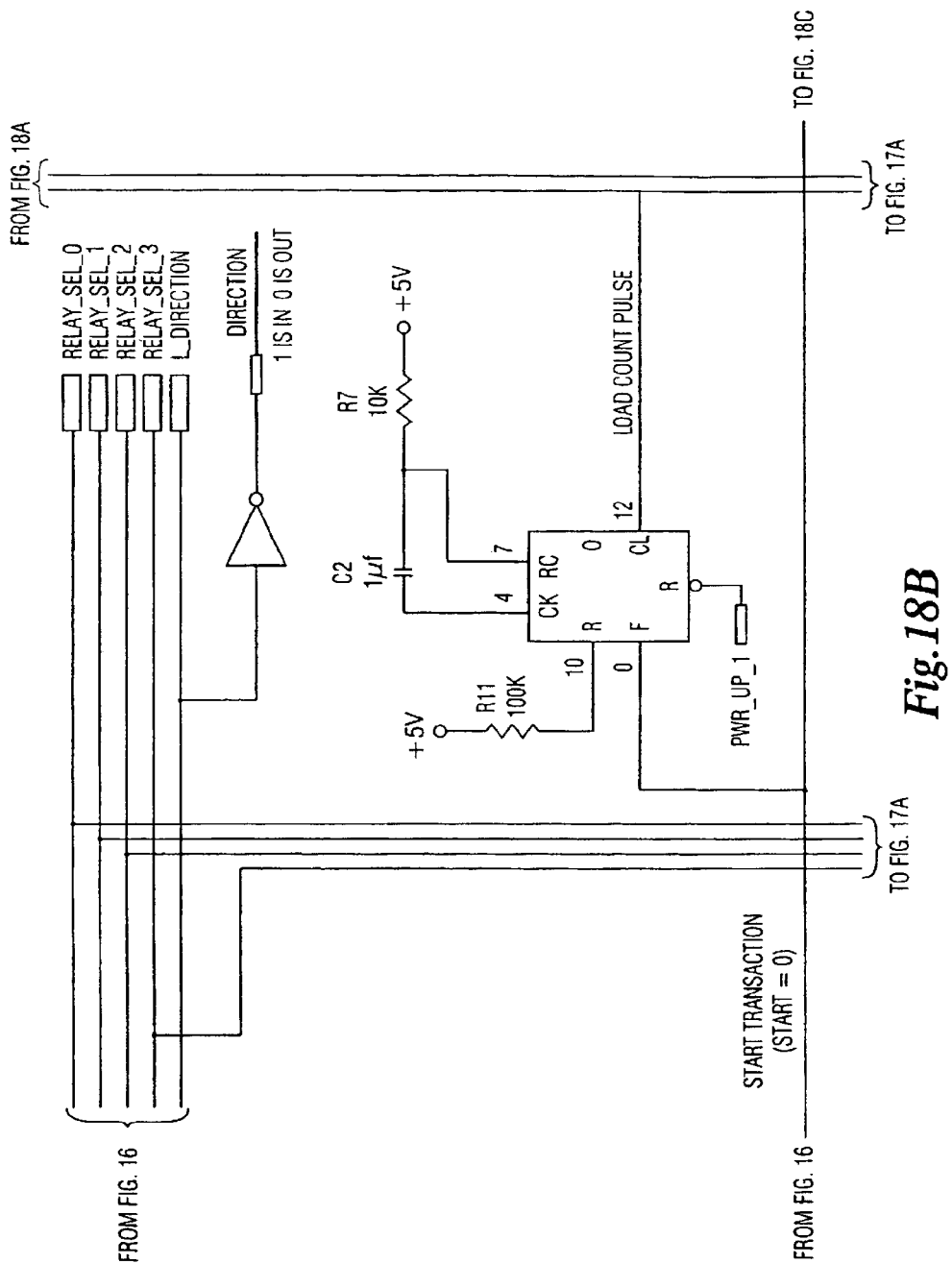
Figure 18C:
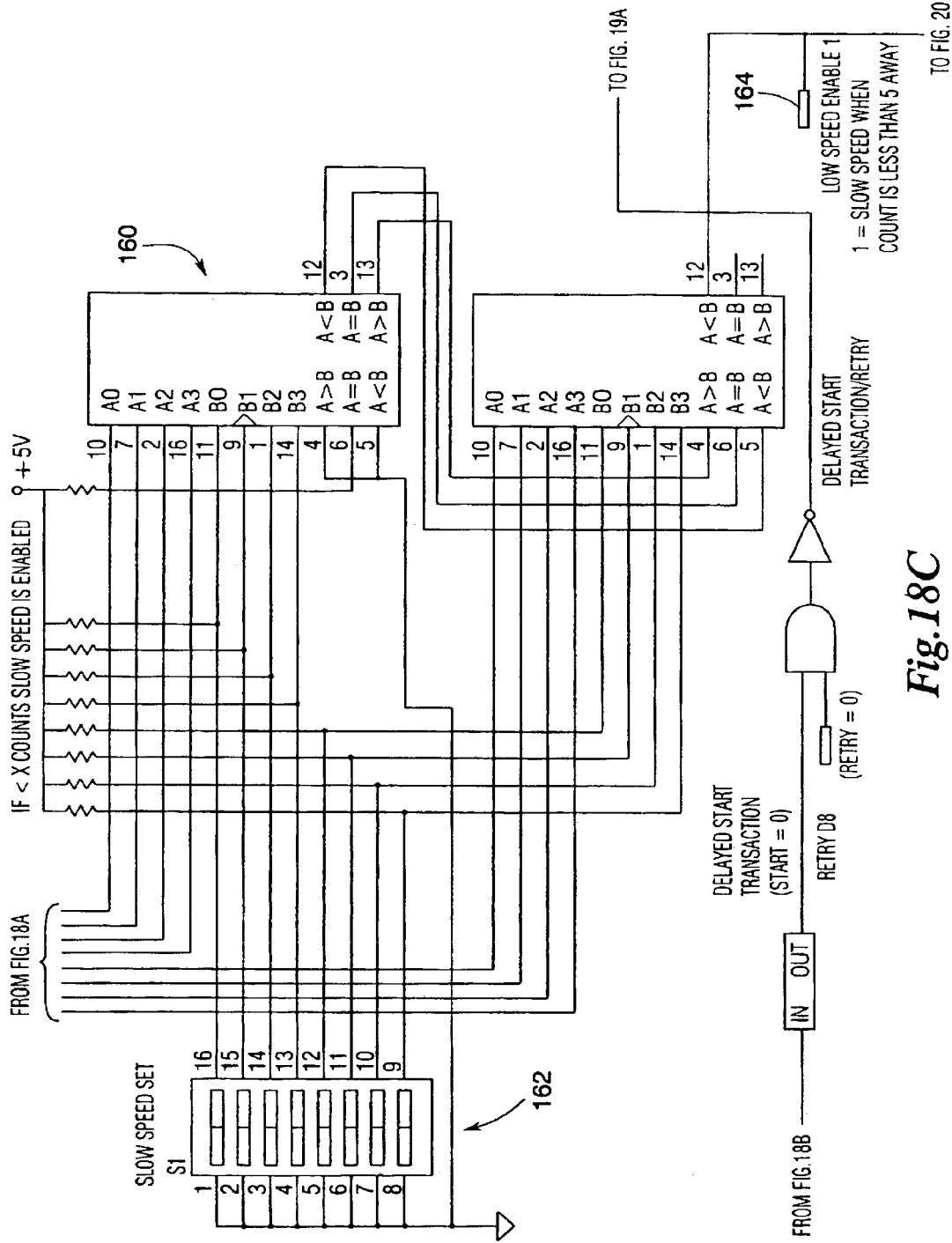

Turning first to FIGS. 16, 17 and 18, two eight bit words are received in the upper left-hand corner of FIG. 16 from the control computer 32. The first eight bit word 150 represents the distance a drawer is to travel. From the second eight bit word, four bits 152 represent a drawer select signal, a bit 154 is representative of a start transaction, a bit 155 is representative of direction, a bit 156 is representative of a "clear error" signal, and a bit 157 is representative of a "retry" signal. The distance bits 150 are input to a counter 158. A comparator 160 is responsive to the counter 158. The comparator 160 is also responsive to a plurality of switches 162 which set a value to which the comparator compares the output of the counter 158.

The counter 158 is loaded with the distance information encoded in the bits 150. The counter 158 then begins counting down from the loaded value. While the counter is counting down, the drawer is being driven at a first, high speed. When the counter reaches the value set by the switches 162, the comparator 160 produces a signal available at node 164 which is referred to as the "low speed enable" signal. This indicates to a circuit, to be described later, that the drawer has traveled a substantial portion of the distance that it is to travel and the speed should now be reduced for the remainder of the distance to be traveled.

The drawer select bits 152 are latched in a latch 166 seen in FIG. 16. The drawer select bits 152 are input, via FIG. 18, to a drive select/control circuit described herein below. The drawer select bits 152 are also input, via FIG. 18, to motor sensor select/clock circuit 168, see FIG. 17, which is used to identify which drawer is to be actuated for purposes of selecting appropriate feedback signals from the actuated drawer.

Figure 19A:
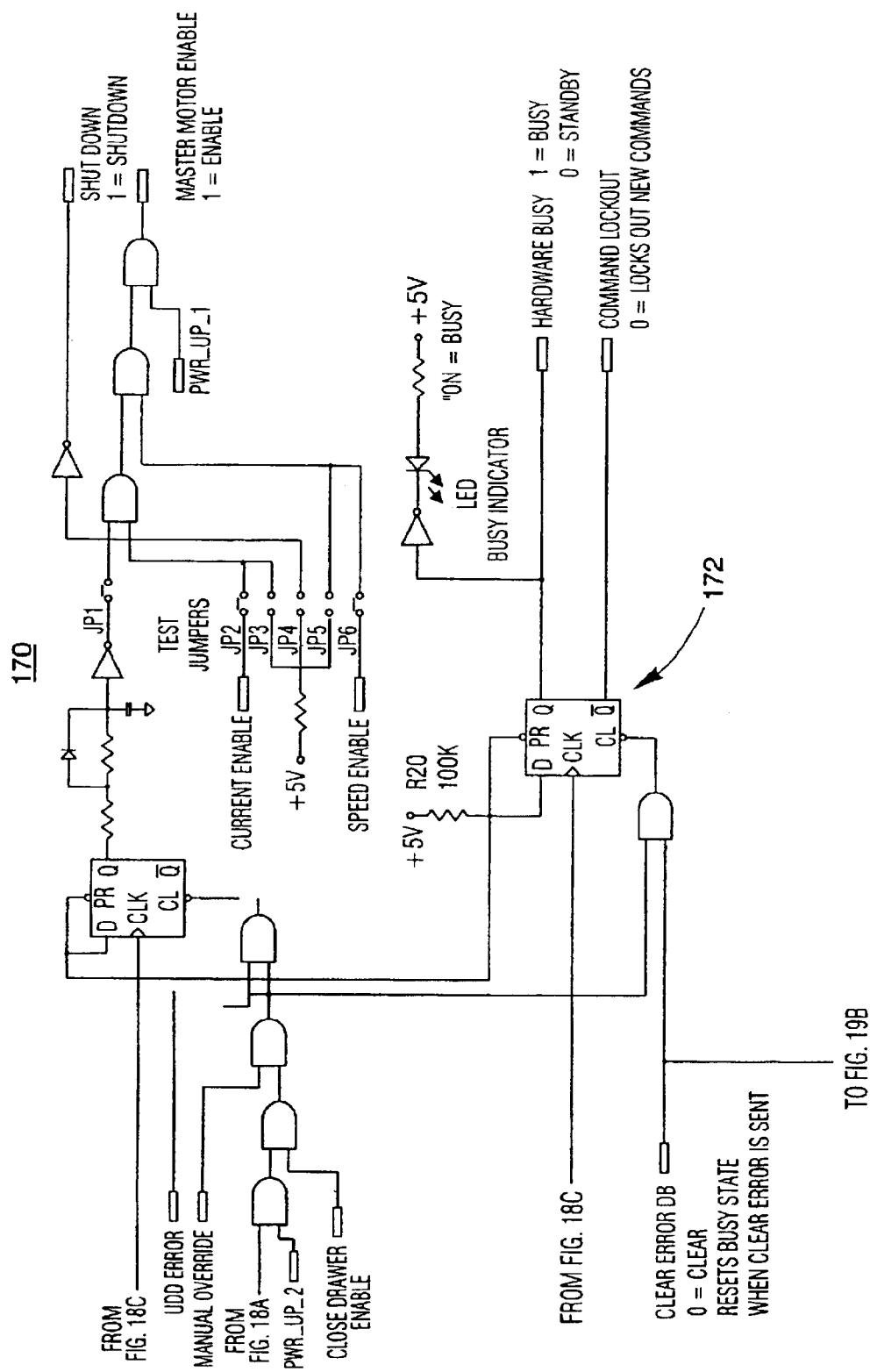
Figure 19B:
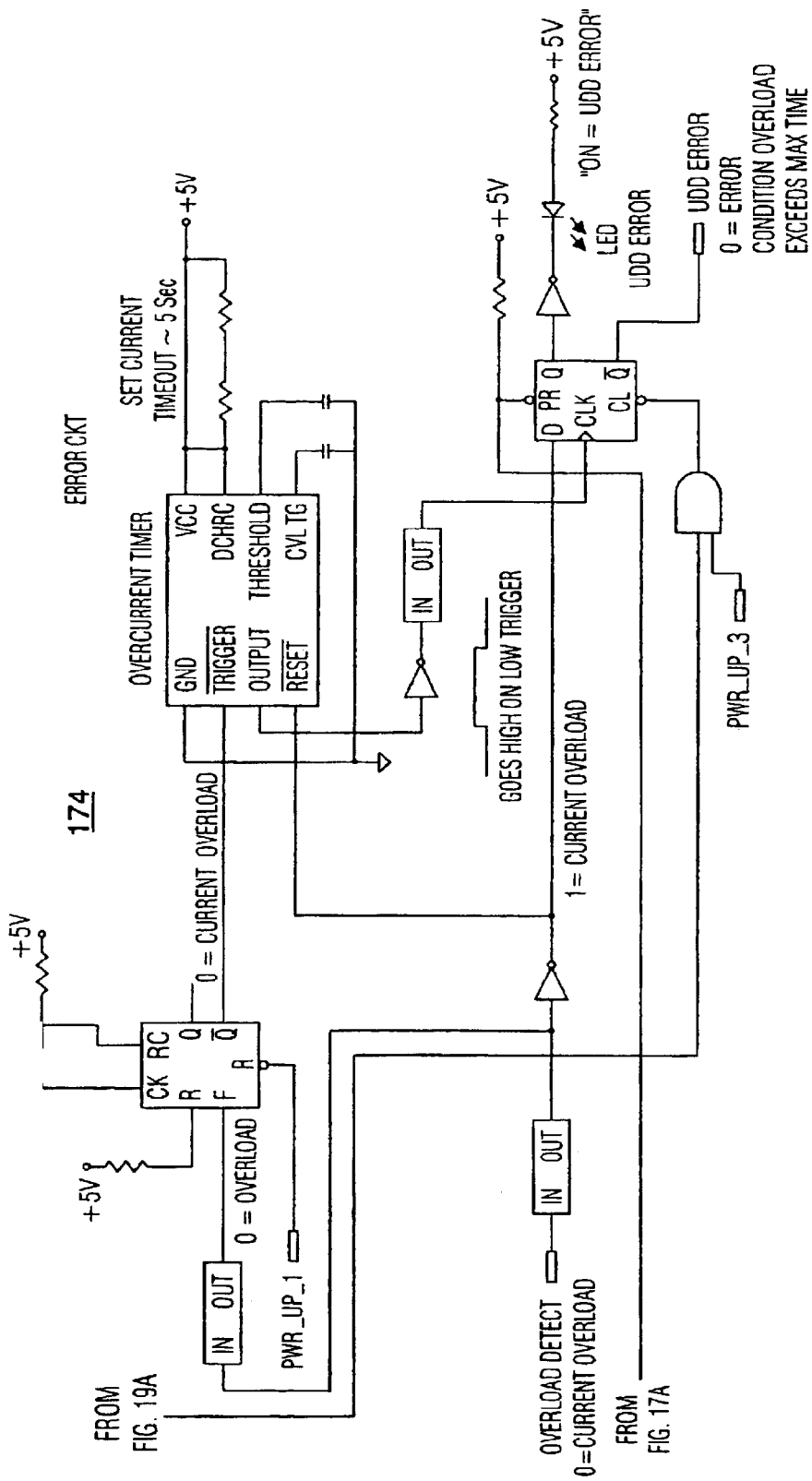

FIG. 19 has in the upper portion thereof a motor enable path 170 which is responsive to a "count complete/enable" signal from FIG. 18 as well as a "delayed start transaction/retry" signal also from FIG. 18. Those two signals are processed as shown in motor enable path 170 to produce a "master motor enable" signal.

In the middle of FIG. 19, a flip-flop 172 is provided which is responsive to the motor enable path 170 as well as the "delayed start transaction/retry" signal available from FIG. 18. The flip-flop 172 produces the signals "hardware busy" and "command lock out".

Finally, in the bottom portion of FIG. 19, a circuit path 174 is provided for producing an "error" signal in response to an "overload detect" signal (indicative of an overcurrent condition) input to the circuit path 174. In response to the detection of an overcurrent condition, the "error" signal is generated.

Figure 20:
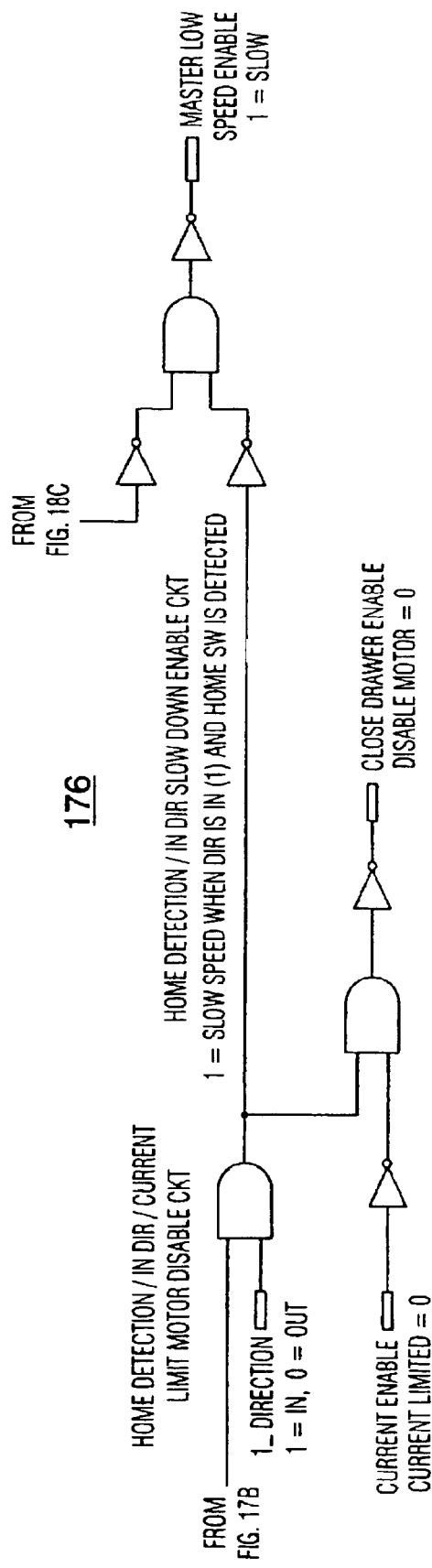

FIG. 20 illustrates a circuit path 176 for producing a "master low speed enable" signal through the logical combination of the "low speed enable signal" produced by the comparator 160 of FIG. 18 and a "drawer open/closed feedback" signal from FIG. 17.

Figure 21A:
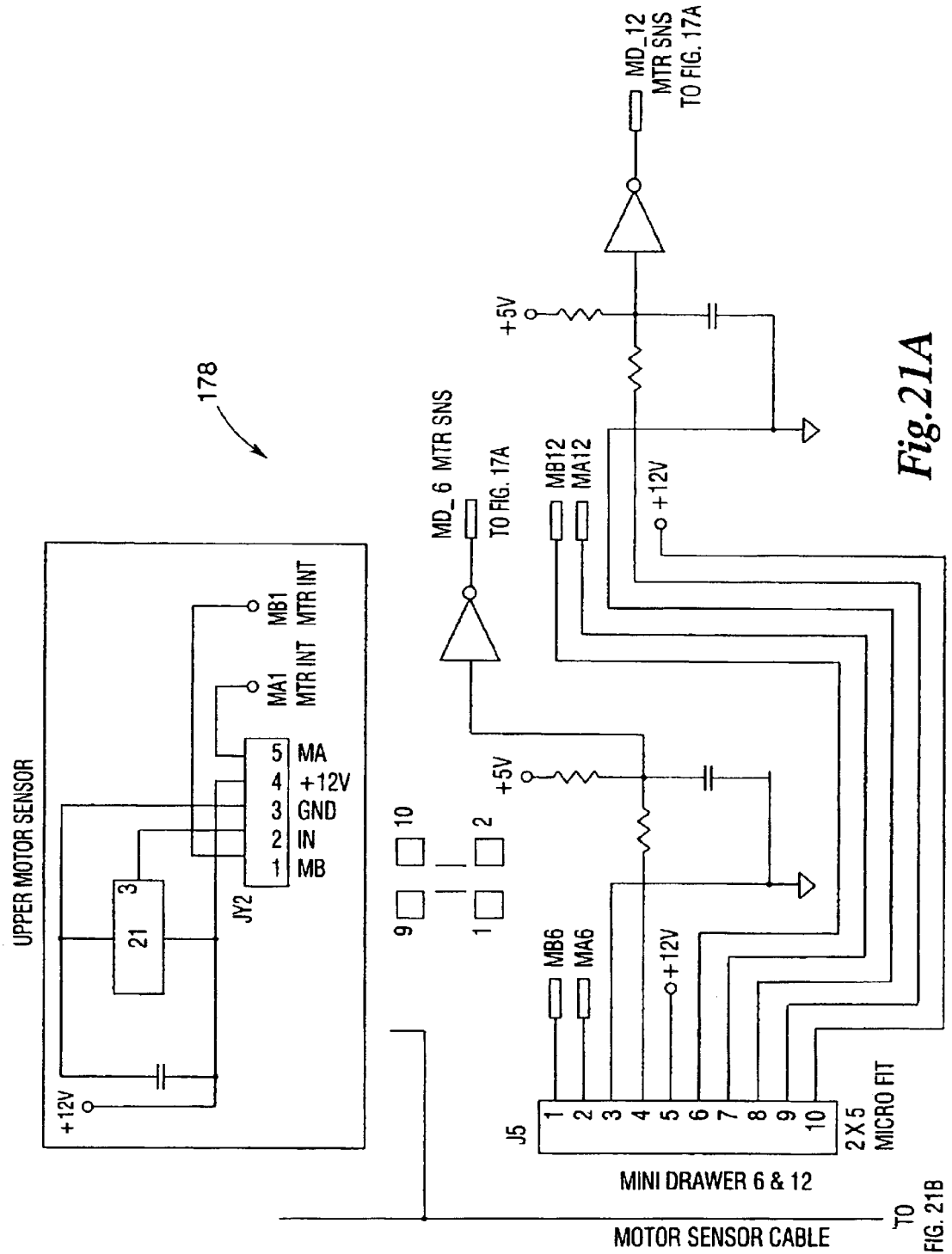
FIG. 21 is an electrical schematic of motor sensor interface electronics.

FIG. 21 illustrates motor sensor interface electronics 178. The motor sensor interface electronics 178 receive the signals produced by the Hall transducers to produce signals MD__1 through MD__12 MTR SNS signals which are input to the motor sense select/clock circuit 168 shown in FIG. 17. In FIG. 21, the motor sensor interface electronics are shown for four of the drawers.

Figure 22:
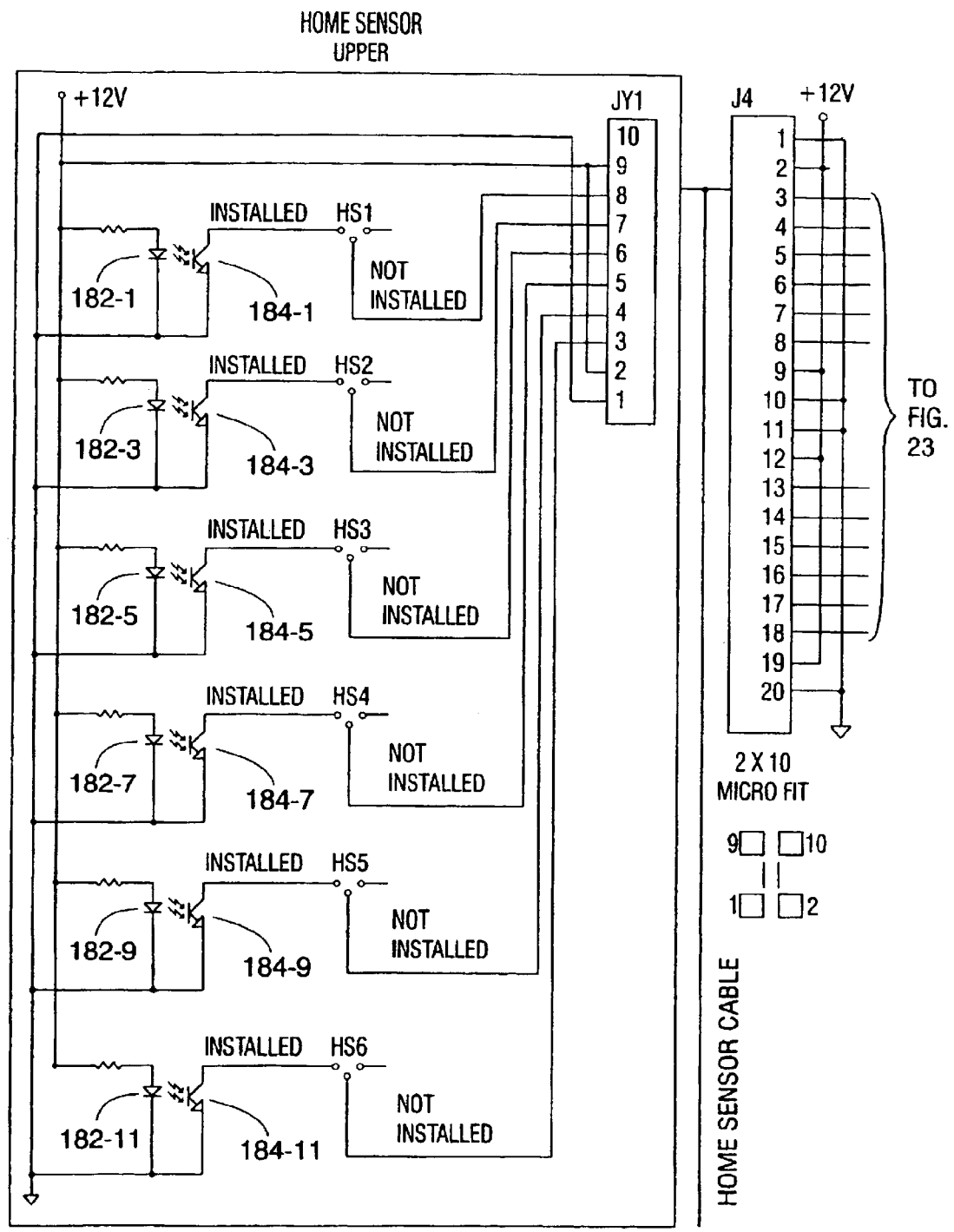
FIGS. 22 and 23 are electrical schematics for home sensor electronics.
Figure 23:
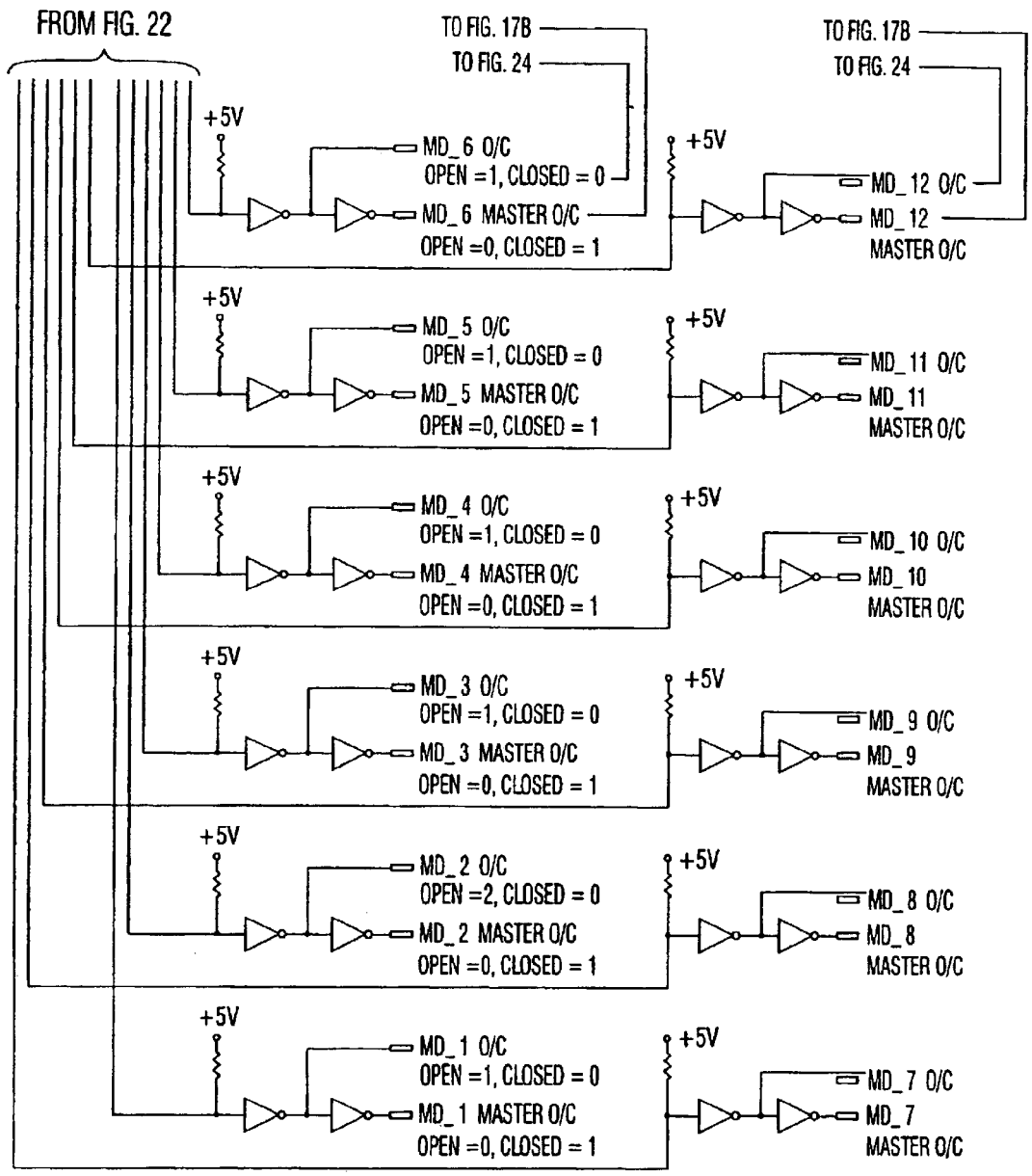

FIG. 22 illustrates home sensor electronics 180 for the upper individual drawers. Each of the trays is provided with an upstanding metal tab or flag (95 in FIG. 7). The drive chassis carries sensors, each sensor comprised of one LED 182-1, 182-3, 182-5, 182-7, 182-9, and 182-11 and one corresponding light sensitive transistor 184-1, 184-3, 184-5, 184-7, 184-9, and 184-11 corresponding to the upper trays 62-1, 62-3, 62-5, 62-7, 62-9, and 62-11, respectively, of which only tray 62-3 is shown in FIG. 11. When each tray 62-1, 62-3, 62-5, 62-7, 62-9, and 62-11 is in its closed or home position, the flag carried by that tray blocks the light produced by the LED 182-1, 182-3, 182-5, 182-7, 182-9, and 182-11 from being received by the corresponding light sensitive transistor 184-1, 184-3, 184-5, 184-7, 184-9, and 184-11, respectively. The signals produced by the sensors 184-1 through 184-12 are input to the logic shown in FIG. 23 to produce MD__1 through MD__12 O/C (open/closed) signals and MD__1 through MD__12 Master O/C signals.

Figure 24:
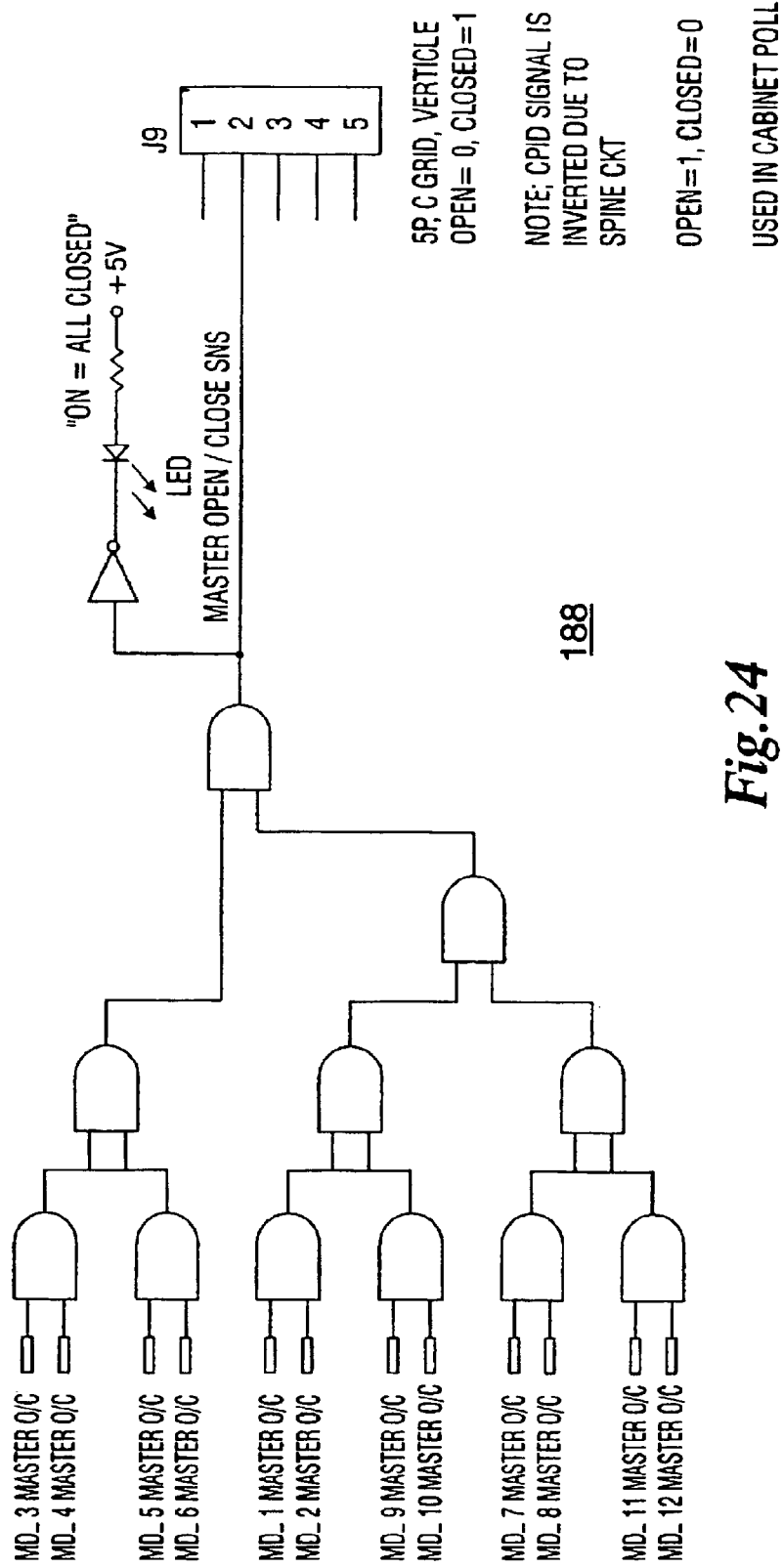
FIG. 24 is an electrical schematic of logic for producing a "Master open/close SNS" signal.

The MD__1 through MD__12 O/C signals are input to the logic circuit 188 illustrated in FIG. 24. The logic circuit 188 combines the signals to produce a "Master open/close SNS" signal. The MD__1 through MD__12 Master O/C signals are input to the motor sensor select/clock circuit 168 illustrated in FIG. 17.

Figure 25:
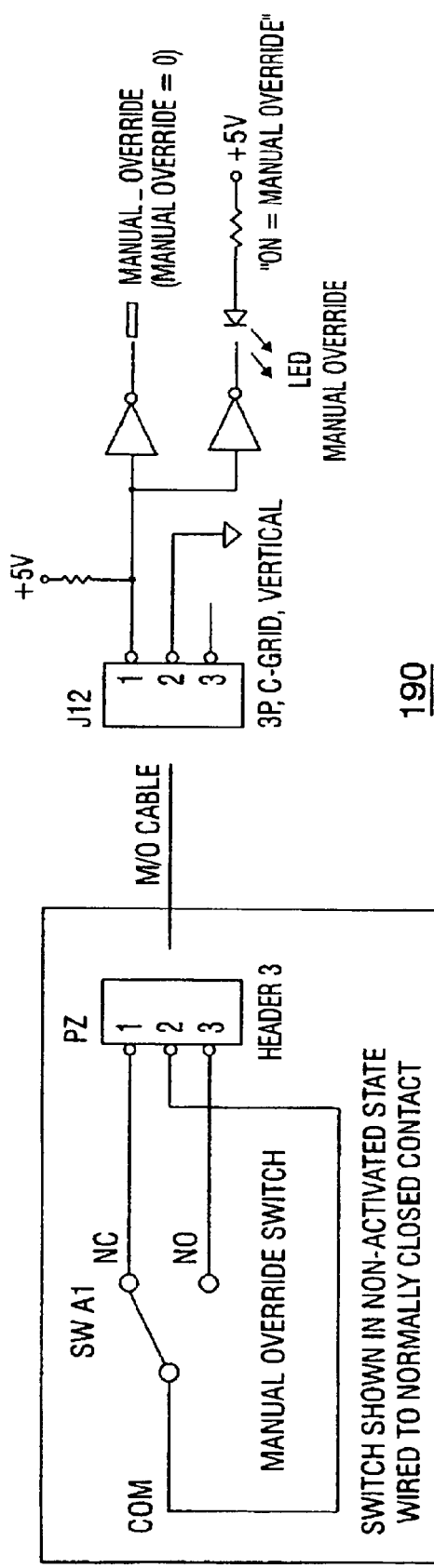
FIG. 25 is an electrical schematic of a manual override circuit.

FIG. 25 illustrates a manual override circuit 190. The manual override circuit 190 is responsive to the position of the override bar 115 to produce a signal indicative of a manual override. When a manual override is in effect, a "Manual Override" signal is produced by the manual override circuit 190 illustrated in FIG. 25.

Figure 26:
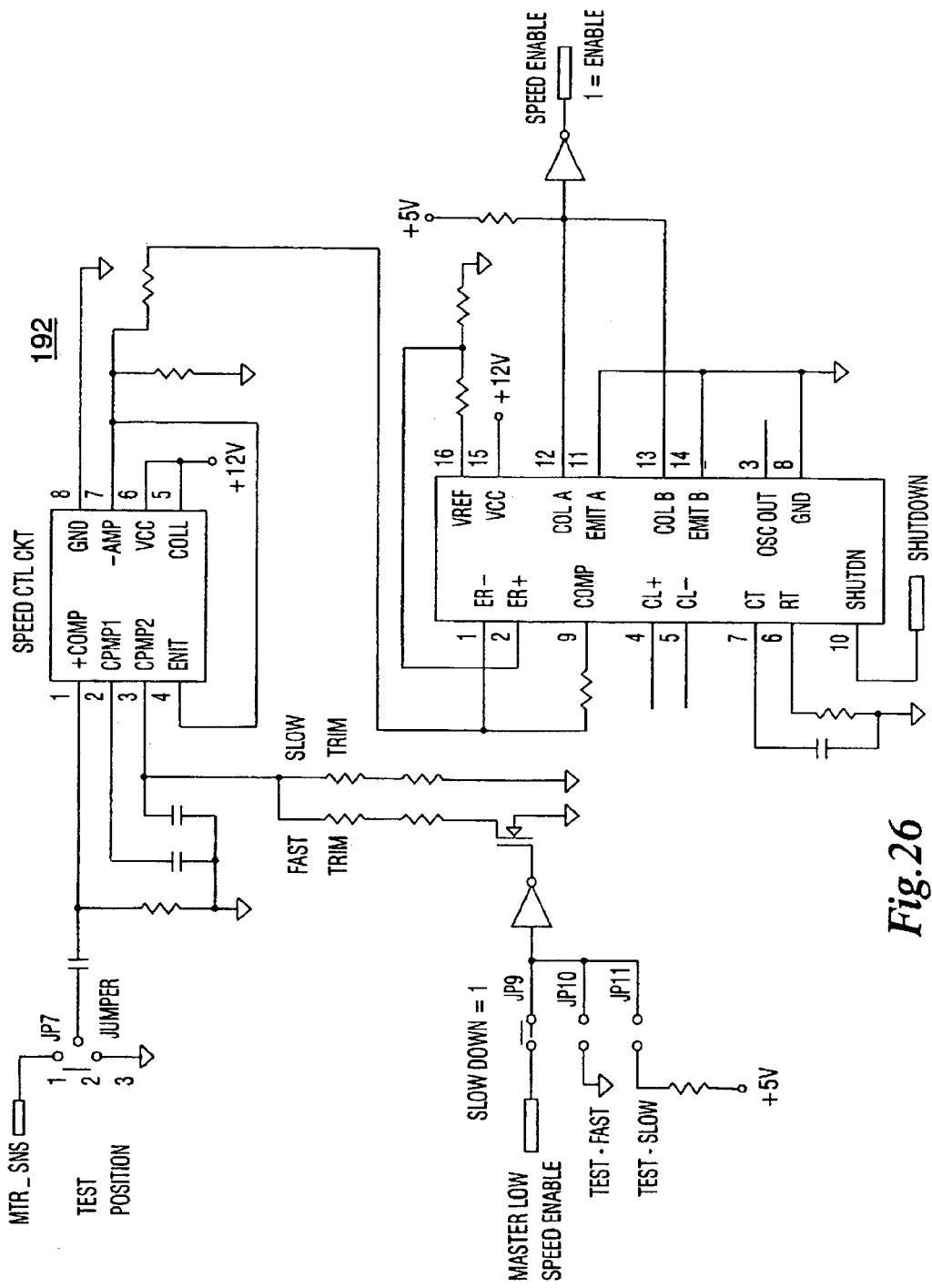
FIG. 26 is an electrical schematic of a speed control circuit.

FIG. 26 illustrates a pulse width modulated speed control circuit 192 responsive to the MTR-SNS signal produced by the motor sense select/clock circuit 168 of FIG. 17. The speed control circuit produces a "speed enable" signal.

Figure 27:
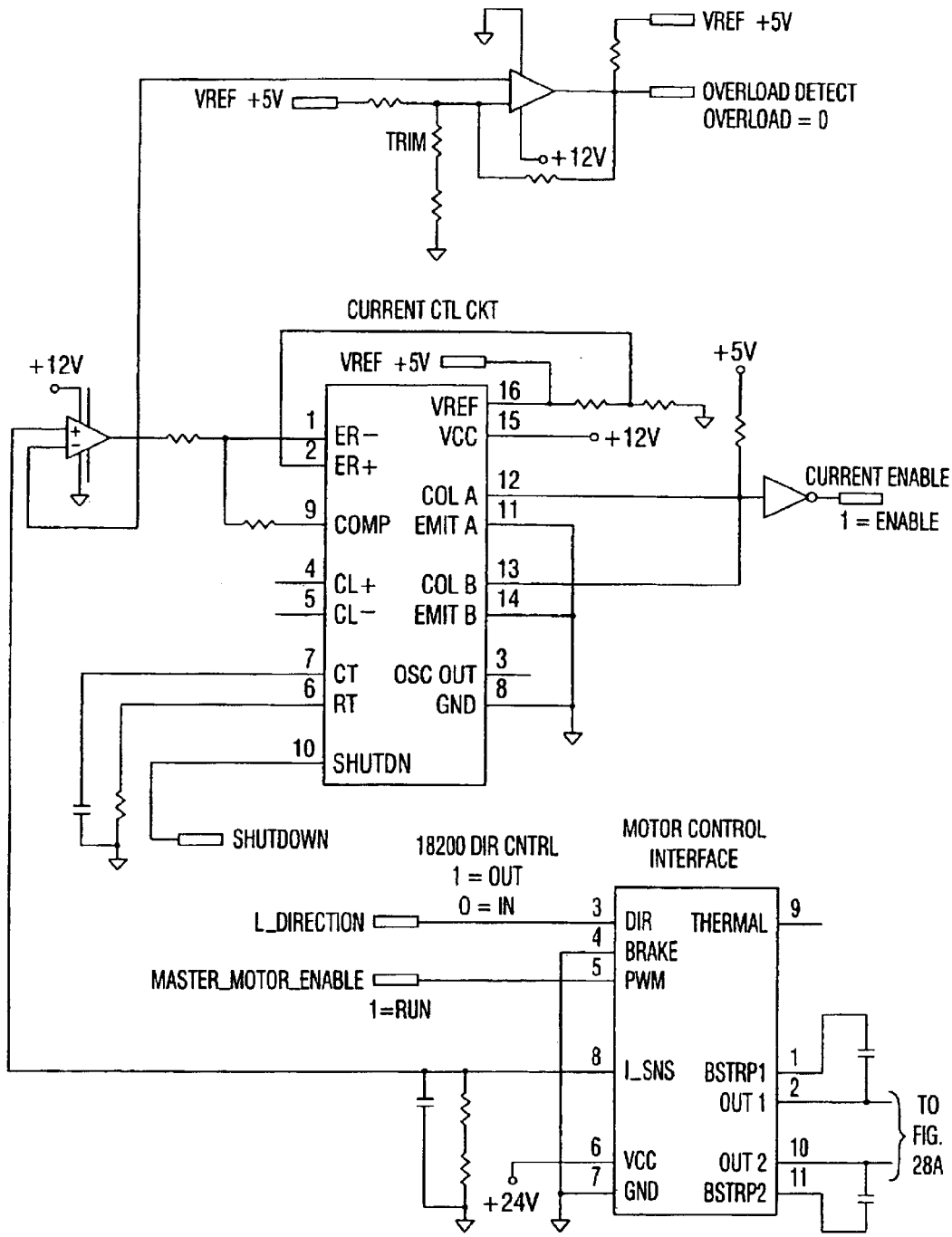
FIG. 27 is an electrical schematic of current control circuit and a motor control interface.
Figure 28A:
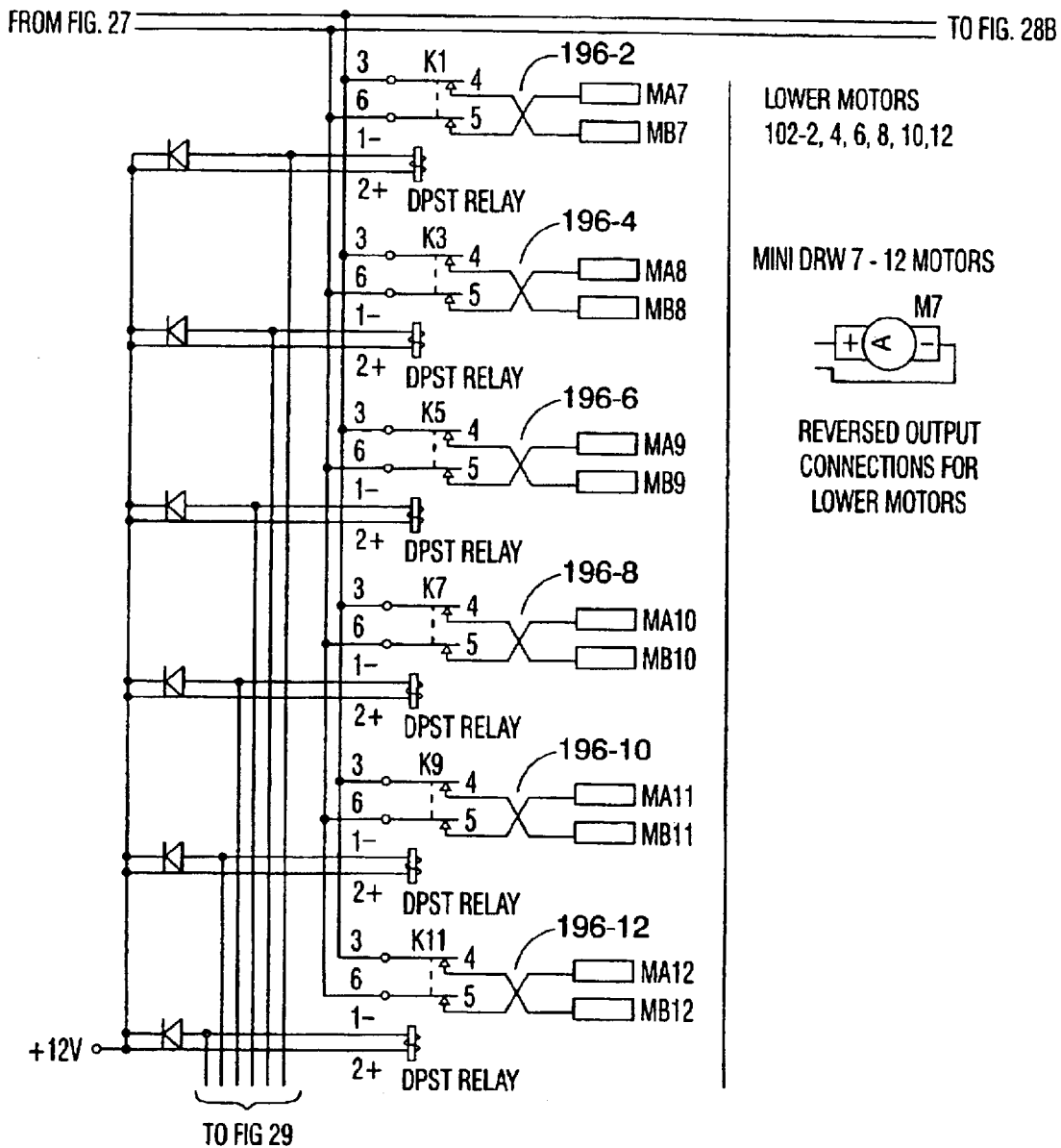
FIGS. 28 and 29 are electrical schematics of a drive select circuit and a plurality of relays used to drive a selected motor.
Figure 28B:
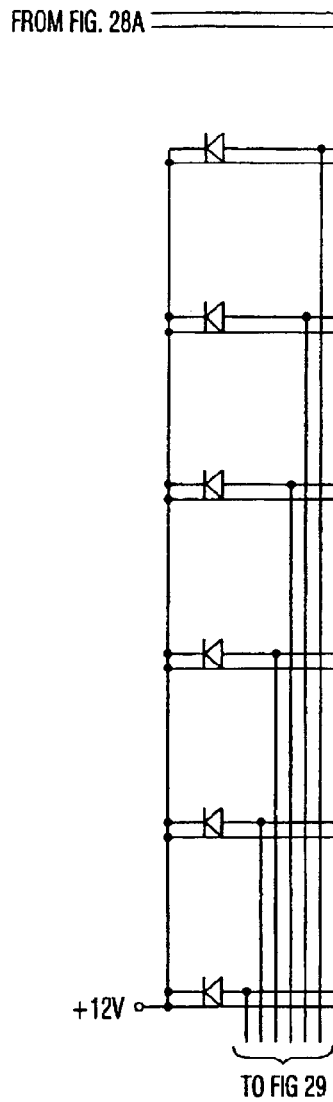
Figure 28B:
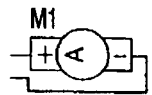
Figure 29:
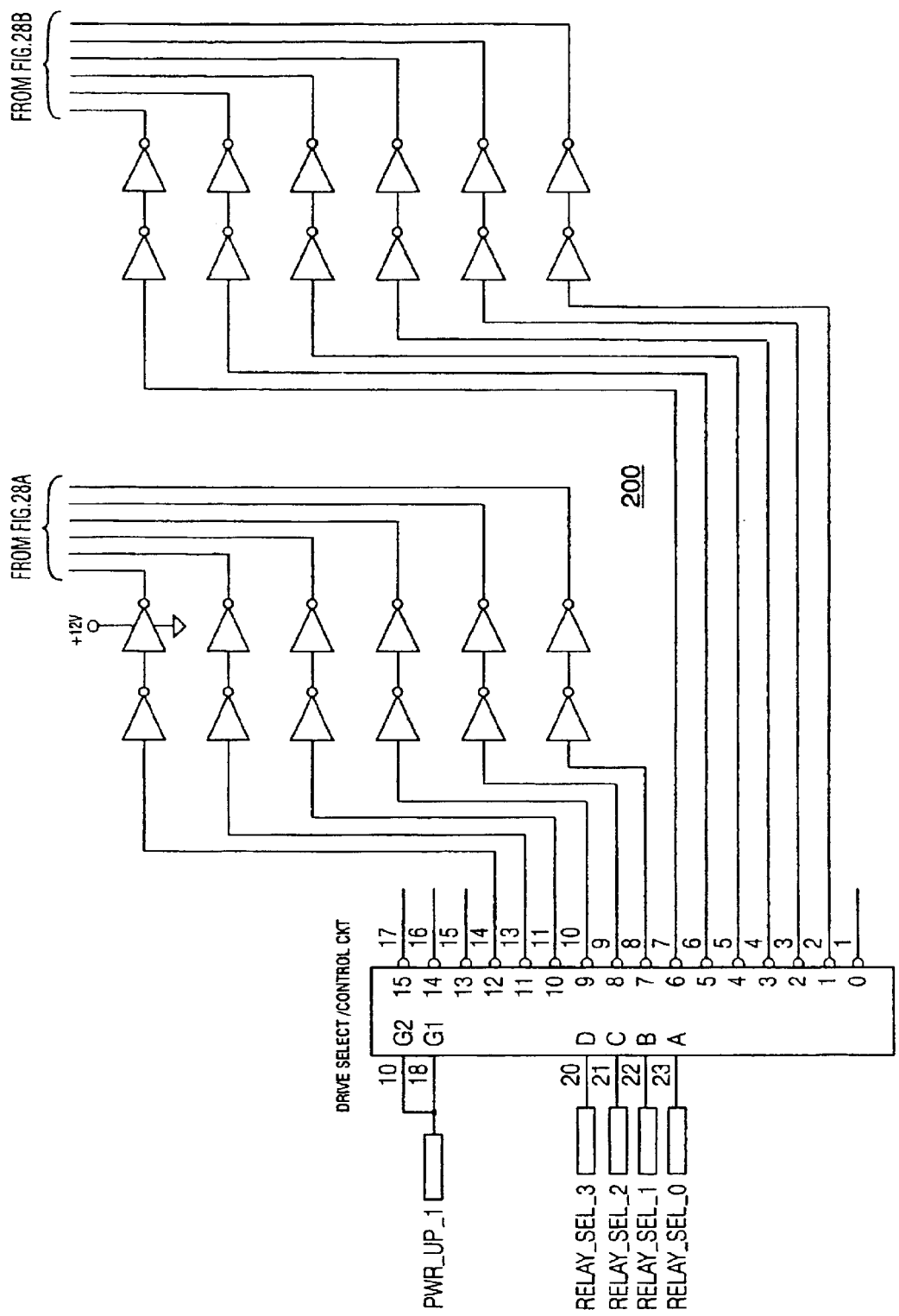

FIG. 27 illustrates in the lower portion a motor control interface 194 producing signals input to relays 196-1 through 196-12 illustrated in FIG. 28. FIG. 27 also illustrates a current control circuit 198. The current control circuit 198 is responsive to an overcurrent condition, e.g., the drawer has run into an obstacle, jammed, or is otherwise having trouble moving, and produces a "current enable" signal. The current enable signal is used to drive the motors up to a maximum overcurrent condition. The current control circuit 198 may be viewed as a force control. More specifically, sufficient force is generated to overcome system friction and mass, but not enough force to injure anyone should they be in the path of a moving drawer. The control computer 32 may be provided with software for providing an automatic retry and an anti-pitch movement whenever a jam is detected. The relays 196-1 through 196-12 of FIG. 28 are responsive to signals produced by the logic circuit 200 illustrated in FIG. 29.

While the present invention has been described in connection with preferred embodiments thereof, those of ordinary skill in the art will recognize that many modifications and variations are possible. The present invention is intended to be limited only by the following claims and not by the foregoing description which is intended to set forth the presently preferred embodiment.

What is claimed is:

1. A method of restocking an individual drawer of a unit dose dispensing drawer, comprising:

opening an individual drawer;

releasing a first insert that defines the volume of said drawer from a tray, said first insert divided into a plurality of compartments each having a front, a back, two lateral sides and a lid connected at one of said lateral sides, said compartments serially arranged along the length of said insert;

connecting a filled insert of the same construction as said first insert to the tray from which the first insert has been removed;

unlocking the lids of the filled insert; and closing said open drawer.

2. The method of claim 1 additionally comprising:

delivering the first insert to a location for filling;

filling the first insert and locking the lids thereof; and delivering the filled first insert to a medication dispensing cabinet.

3. The method of claim 1 wherein said unlocking comprises one of a mechanical unlocking or unsealing.

4. The method of claim 1 wherein said opening includes driving the drawer to a fully open position to enable access to a release mechanism.

5. A method of restocking a unit dose drawer comprising:

filling a first insert at a centralized storage location with items to be dispensed, said insert divided into a plurality of compartments each having a front, a back, two lateral sides and a lid connected at one of said lateral sides, said compartments serially arranged along the length of said insert;

sealing the plurality of lids;

delivering said first insert to a decentralized location;

opening an individual drawer of a unit dose dispensing drawer to its fully open position;

removing an insert from said individual drawer;

placing said first insert into the position previously occupied by said removed insert; and closing said open drawer.

6. A method of controlling the operation of a unit dose dispensing drawer having a plurality of individual drawers, comprising:

in the case of a controlled item, opening an individual drawer only a distance needed to dispense an indicated quantity of an identified controlled item; and in the case of a non-controlled item, opening an individual drawer to its fully open position to dispense an indicated quantity of an identified non-controlled item.

* * * * *